US009155300B2

(12) United States Patent
Feng et al.

(10) Patent No.: US 9,155,300 B2
(45) Date of Patent: Oct. 13, 2015

(54) METHODS AND COMPOSITIONS FOR IMPROVING PLANT HEALTH

(75) Inventors: Paul C.C. Feng, Wildwood, MO (US); Ronald J. Brinker, Ellisville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 395 days.

(21) Appl. No.: 13/475,906

(22) Filed: May 18, 2012

(65) Prior Publication Data
US 2013/0244875 A1    Sep. 19, 2013

Related U.S. Application Data

(60) Division of application No. 12/099,101, filed on Apr. 7, 2008, now Pat. No. 8,207,092, which is a continuation-in-part of application No. PCT/US2007/081527, filed on Oct. 16, 2007.

(60) Provisional application No. 60/852,308, filed on Oct. 16, 2006.

(51) Int. Cl.
*A01N 37/40* (2006.01)
*A01H 3/04* (2006.01)
*C12N 15/82* (2006.01)
*A01N 43/36* (2006.01)
*A01N 47/10* (2006.01)

(52) U.S. Cl.
CPC ............... *A01N 37/40* (2013.01); *A01H 3/04* (2013.01); *C12N 15/8261* (2013.01); *C12N 15/8271* (2013.01); *C12N 15/8274* (2013.01); *C12N 15/8275* (2013.01); *C12N 15/8281* (2013.01); *C12N 15/8282* (2013.01); *C12N 15/8285* (2013.01)

(58) Field of Classification Search
CPC ............................ A01N 37/40; C12N 15/8271
USPC ........................................................ 504/206
See application file for complete search history.

(56) References Cited

U.S. PATENT DOCUMENTS

| | | | |
|---|---|---|---|
| 3,619,169 A | 11/1971 | Zick | |
| 5,637,553 A | 6/1997 | Lehs et al. | |
| 5,670,706 A | 9/1997 | Cornelissen et al. | |
| 6,764,854 B2 | 7/2004 | Konzak et al. | |
| 7,012,040 B2 | 3/2006 | Hacker | |
| 7,022,896 B1 | 4/2006 | Weeks et al. | |
| 7,105,724 B2 | 9/2006 | Weeks et al. | |
| 7,230,163 B2 | 6/2007 | Becton et al. | |
| 7,812,224 B2 | 10/2010 | Weeks et al. | |
| 7,855,326 B2 | 12/2010 | Feng | |
| 8,207,092 B2 | 6/2012 | Bhatti | |
| 8,859,846 B2 | 10/2014 | Barton et al. | |
| 2002/0094934 A1 | 7/2002 | Hacker | |
| 2003/0115626 A1 | 6/2003 | Weeks et al. | |
| 2003/0135879 A1 | 7/2003 | Weeks et al. | |
| 2005/0249667 A1 | 11/2005 | Tuszynski et al. | |
| 2006/0265780 A1 | 11/2006 | Prosch et al. | |
| 2008/0119361 A1 | 5/2008 | Feng | |
| 2009/0105077 A1 | 4/2009 | Bhatti | |
| 2014/0315717 A1 | 10/2014 | Bhatti et al. | |

FOREIGN PATENT DOCUMENTS

| | | |
|---|---|---|
| RU | 2226215 | 3/2004 |
| WO | WO 98/09525 | 3/1998 |
| WO | WO 2004/057957 | 7/2004 |
| WO | WO 2005/102057 | 11/2005 |
| WO | WO 2007/143690 | 12/2007 |
| WO | WO 2007/146706 | 12/2007 |
| WO | WO 2008/048964 | 4/2008 |

OTHER PUBLICATIONS

"Banvel Herbicide" Product Insert, undated.
Thompson et al., "Soybean Tolerance to Early Preplant Applications of 2,4-D Ester, 2,4-D Amine, and Dicamba," *Weed Technology*, 21:882-885, 2007.
USPTO: Non-final Office Action for U.S. Appl. No. 12/440,173 dated Jan. 29, 2013.
Official Action date-mailed Feb. 14, 2011 in Eurasian Patent Application No. 200970388.
Response to Non-Final Office Action for U.S. Appl. No. 12/440,173, dated Oct. 8, 2012.
Response to Non-Final Office Action for U.S. Appl. No. 12/440,173, dated May 21, 2013.
USPTO; Final Office Action for U.S. Appl. No. 12/440,173, dated Sep. 16, 2013.
Response to Final Office Action for U.S. Appl. No. 12/440,173, dated Dec. 3, 2013.
USPTO; Notice of Allowance for U.S. Appl. No. 12/440,173, dated Jan. 10, 2014.
U.S. Appl. No. 14/229,611, filed Mar. 28, 2014, Bhatti et al.
Final Office Action regarding U.S. Appl. No. 13/475,909, dated Mar. 13, 2015.
Response to Non-Final Office Action regarding U.S. Appl. No. 13/475,909, filed Nov. 21, 2014.
U.S. Appl. No. 13/475,909, May 18, 2012, Feng.
U.S. Appl. No. 13/475,915, May 18, 2012, Feng.
Article entitled "Swapping Striga for patents", *Grain*, pp. 14-18, Oct. 26, 2006.

(Continued)

*Primary Examiner* — Sue Liu
*Assistant Examiner* — Andriae M Holt
(74) *Attorney, Agent, or Firm* — Dentons US LLP; Pamela J. Sisson

(57) ABSTRACT

The present invention provides methods and compositions for improving plant health. In particular, application of dicamba or another substrate of DMO, or metabolites thereof including DCSA, to a plant confers tolerance to, or defense against, abiotic or biotic stresses such as oxidative stress including herbicide application, and plant disease, and enhances crop yield. Such application may be in combination with the application of another herbicide such as glyphosate.

14 Claims, 11 Drawing Sheets

(56) References Cited

OTHER PUBLICATIONS

English translation of Article entitled "Welcome to Biodiversidad en Amërica Latina y el Caribe".

Behrens et al., "Dicamba resistance: enlarging and preserving biotechnology-based weed management strategies," *Science*, 316:1185-1188, 2007.

Bohner, "Yellow Flash in Soybean," *Ontario Ministry of Agriculture Food and Rural Affairs*, Jun. 29, 2006.

Grossmann, "Mode of action of auxin herbicides: a new ending to long, drawn out story," *Trends Plant Sci.*, 5:506-508, 2000.

Herman, "A three-component dicamba O-demethylase from pseudomonas maltophila, strain, DI-6," *J. of Biological Chem.*, 280(26):24759-24767, 2005.

Kogel et al., "Resistance in barley against the powdery mildew fungus (*Erysiphe graminis f*.sp. *hordei*) is not associated with enhanced levels of endogenous jasmonates," *European Journal of Plant Pathology*, 101:319-332, 1995.

Krueger et al., "Use of dicamba-degrading microorganisms to protect dicamba susceptible plant species," *J. Agric. Food Chem.*, 39:1000-1003, 1991.

Pinheiro, "2, 4-D Hell: From Vietnam's War to War Agriculture," *RAP-AL Uruguay*, http://webs.chasque.net/~rapaluy1/24D/24D.htm, 2004.

Uknes et al., "Acquired resistance in arabidopsis," *The Plant Cell*, 4:645-656, 1992.

Wang et al., In: Characterization of Cellular and Enzymatic Degradation of Dicamba by *Pseudomonas maltophilia*, Strain DI-6, Ph.D. Thesis, University of Nebraska-Lincoln, 1996.

Weeks et al., "Genetic engineering of tobacco, tomato, arabidopsis, and soybean plants for tolerance to treatment with the herbicide dicamba," Soy/2006, 11th Biennial Conference on the Molecular and Cellular Biology of the Soybean (abstr.), University of Nebraska-Lincoln, Lincoln, NE, 2006.

USPTO: Non-final Office Action for U.S. Appl. No. 12/440,173, dated Jul. 24, 2012.

USPTO: Non-Final Office Action regarding U.S. Appl. No. 13/475,909, dated Oct. 6, 2014.

Foy et al., "The Physiology of Metal Toxicity in Plants," *Ann. Rev. Plant Physiol.* 29:511-566, 1978.

Hall, "Cellular mechanisms for heavy metal detoxification and tolerance," *J. Experimental Botany* 53(366):1-11, 2002.

Marksman Herbicide Label and Booklet, 2004, BASF, pp. 1-16.

Isom et al., "The Effects of Five Herbicides Applied at Five Difference Growth Stages of Anza Wheat," *Proceedings of the Western Society of Weed Science* 30:47-50, 1997.

Singh et al., "Broad spectrum weed control in wheat by use of combination of herbicides," *Indian Journal of Agronomy* 31(3):273-279, 1986 (Abstract).

Response to Non-Final Office Action regarding U.S. Appl. No. 14/229,611, dated Jun. 24, 2015.

Response to Final Office Action regarding U.S. Appl. No. 13/475,909, dated Jun. 24, 2015.

USPTO: Non-Final Office Action regarding U.S. Appl. No. 13/475,915, dated Jul. 24, 2015.

Non-Final Office Action regarding U.S. Appl. No. 14/299,611, dated May 1, 2015.

dicamba 3,6-DCSA

SEQUENCE LISTING

<160> NUMBER OF SEQ ID NOS: 2

<210> SEQ ID NO 1
<211> LENGTH: 340
<212> TYPE: PRT
<213> ORGANISM: Artificial Sequence
<220> FEATURE:
<223> OTHER INFORMATION: Synthetic Peptide

<400> SEQUENCE: 1

```
Met Ala Thr Phe Val Arg Asn Ala Trp Tyr Val Ala Ala Leu Pro Glu
 1               5                  10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340
```

```
<210> SEQ ID NO 2
<211> LENGTH: 1023
<212> TYPE: DNA
<213> ORGANISM: Artificial Sequence
<220> FEATURE:
<223> OTHER INFORMATION: Synthetic Primer

<400> SEQUENCE: 2
atggccacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg gccatctcca atgccctat cacgggctgg aattcgatgg cggcgggcag      240
tgcgtccata acccgcacgg caatggcgcc cgcccggctt cgctcaacgt ccgctccttc     300
ccggtggtgg agcgcgacgc gctgatctgg atctgtcccg gcgatccggc gctggccgat     360
cctggggcga tccccgactt cggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct tcgaccggct ggagcgcgag     540
gtgatcgtcg gcgacggtga gatacaggcg ctgatgaaga ttcccggcgg cacgccgagc     600
gtgctgatgg ccaagttcct gcgcggcgcc aatacccccg tcgacgcttg gaacgacatc     660
cgctggaaca aggtgagcgc gatgctcaac ttcatcgcgg tggcgccgga aggcaccccg     720
aaggagcaga gcatccactc gcgcggtacc catatcctga cccccgagac ggaggcgagc     780
tgccattatt tcttcggctc ctcgcgcaat ttcggcatcg acgatccgga gatggacggc     840
gtgctgcgca gctggcaggc tcaggcgctg gtcaaggagg acaaggtcgt cgtcgaggcg     900
atcgagcgcc gccgcgccta tgtcgaggcg aatggcatcc gcccggcgat gctgtcgtgc     960
gacgaagccg cagtccgtgt cagccgcgag atcgagaagc ttgagcagct cgaagccgcc    1020
tga                                                                    1023
```

METHODS AND COMPOSITIONS FOR IMPROVING PLANT HEALTH

This application is a divisional of U.S. patent application Ser. No. 12/099,101, filed Apr. 7, 2008, which is a continuation-in-part of International Application No. PCT/US2007/081527, filed Oct. 16, 2007, which claims the priority of U.S. Provisional Application Ser. No. 60/852,308 filed Oct. 16, 2006, all of which are incorporated herein by reference.

BACKGROUND OF THE INVENTION

1. Field of the Invention

The invention relates generally to the field of agriculture. More specifically, the invention relates to methods for improving plant health by application of dicamba herbicide and/or metabolites or analogs thereof to plants.

2. Description of Related Art

Dicamba (3,6-dichloro-o-anisic acid or 3,6-dichloro-2-methoxybenzoic acid; FIG. 7), active ingredient in herbicides such as Banvel® (BASF), Clarity® (BASF), and Vanquish® (Syngenta), is a potent herbicide. Although its precise mechanism of activity is unclear, it appears to act as a plant growth regulator (e.g. Grossmann 2000). Its application results in uncontrolled growth, leaf curling and twisting, chloroplast damage, and direct phytotoxic effects, among others. Some of these effects are believed to be caused by ethylene synthesis, which triggers an increase in the biosynthesis of abscisic acid, another plant hormone. Thus imbalances in plant hormone levels appear to underlie the toxic effects.

A dicamba monooxygenase (DMO), has been found to confer tolerance to dicamba by degrading it to 3,6-dichloro salicylic acid (DCSA; 3,6-DCSA; FIG. 7) in bacteria (e.g. Herman et al., 2005; US Patent Publ. 20060168700; U.S. Pat. No. 7,022,896). The DMO gene has subsequently been used to confer tolerance to Dicamba in soybean and other plants (e.g. Weeks et al., 2006). These new dicamba-tolerant crops allow for applications of dicamba on crops which were previously extremely sensitive to any dicamba exposure, particularly dicots such as cotton, canola, and soybean.

U.S. Pat. No. 7,230,163 describes a method of improving crop yields by application of a synthetic auxin to a plant. However, plant health, e.g. resistance to biotic or abiotic stress, is not addressed, nor is the effect of metabolites of the applied auxin.

As in planta metabolism is generally unpredictable, i.e., one cannot predict from prior traditional uses of dicamba (e.g., on corn not expressing a DMO gene) what metabolites might result from the use of dicamba in new dicamba-tolerant crops expressing DMO, or the effects of such metabolites in the plant. The present inventors have found that in these DMO-expressing crops, DMO detoxifies dicamba and produces dicamba metabolites, including DCSA. Unexpectedly, the present inventors have also discovered that this DCSA metabolite confers beneficial health effects on the plants. Accordingly, the present invention is directed to, among other things, methods of improving plant health using dicamba metabolites, including DCSA, and the plants, seeds, and crops resulting therefrom.

These improvements in plant health provide increased resistance of plants against biotic (e.g., insects, fungi, viruses, nematodes, and other pathogens) and abiotic stresses (e.g., drought, cold, ozone, soil nutrient deficiencies), with resulting increases in yields and improved quality of crops, all of which will be a great benefit to agriculture.

SUMMARY OF THE INVENTION

In one aspect, the invention provides a method for improving the health of a plant, comprising providing the plant with dicamba, or a product of DMO-mediated metabolism or analog thereof, in an amount that improves the health of the plant as compared to a plant of the same genotype not provided with the dicamba or product of DMO-mediated metabolism or analog thereof. In one embodiment, the invention provides a method for improving the health of a plant, comprising contacting the plant with dicamba or a product of DMO-mediated metabolism thereof to provide the plant with a product of DMO-mediated metabolism of dicamba in an amount that improves the health of the plant as compared to a plant of the same genotype not provided with the dicamba or product of DMO-mediated metabolism thereof, wherein a plant contacted with dicamba comprises DMO.

In one embodiment, the plant is in a crop production field. The method may further comprise allowing the plant to be subject to biotic or abiotic stress prior to, concurrently with or after providing the plant with the dicamba or a product of DMO-mediated metabolism or analog thereof. The method may also further comprise the step of identifying the plant as in need of improved plant health prior to providing the plant with the dicamba or a product of DMO-mediated metabolism or analog thereof.

In one embodiment, identifying the plant as in need of improved plant health comprises identifying the plant as comprising at least a first symptom indicative of biotic or abiotic stress. In specific embodiments, the symptom is selected from the group consisting of stunting, loss of photosynthetic function, lipid peroxidation, accumulation of active oxygen species, increase in free radical content, and tissue necrotization (also termed the "hypersensitive response"). In a particular embodiment, the plant displays a symptom of stunting. The plant identified as in need of improved health may be an immature plant undergoing vegetative growth and sensitive to a disease or to weed growth. In particular embodiments, the plant is a soybean plant in growth stage VE to V3, a cotton plant prior to $1^{st}$ square formation, or a corn plant prior to or during growth stages VE to VT.

The plant health of which is improved according to the invention may be at risk for or under abiotic stress. Examples of abiotic stress include osmotic stress, heat or cold exposure, oxidative stress and nutrient deficit. In a particular embodiment, the plant is at risk for or under osmotic stress, such as drought stress. In another embodiment, the plant is at risk for or under oxidative stress, such as due to application of an herbicide, or due to the presence of ozone at a level that can injure a plant.

Such a plant may also be defined as at risk for or under biotic stress. Examples of biotic stress include fungal disease such as Soybean Rust, viral disease, bacterial disease, insect infestation, nematode infestation, and weed infestation. In one embodiment, the plant is at risk for or under the stress of fungal disease. In a particular embodiment, the plant is at risk for or under the stress of Soybean Rust. In another embodiment, the plant is at risk for or under the stress of weed infestation. Weed infestation constitutes a stress to a crop, especially to young plants such as soybean plants up to growth stage V3-V4.

In a method of the invention, tolerance to oxidative stress in a plant may be increased. A method of the invention may also comprise providing a population of plants with the dicamba or a product of DMO-mediated metabolism or analog thereof to improve the health of the plants, for instance by metabolism of dicamba to DCSA. If dicamba is applied, this may be at a rate which is not herbicidal, yet results in a plant health benefit due to metabolism of dicamba to DCSA, or other product of plant metabolism of dicamba or DCSA.

In a method of the invention, the product of DMO-mediated metabolism may be defined as one or more of 3,6-DCSA, 3,5-DCSA, or 3-CSA, or a metabolite of 3,6-DCSA, 3,5-DCSA, and 3-CSA. The dicamba, applied product of DMO-mediated metabolism, or a metabolite, may be herbicidal. The plant may comprise a transgene that encodes DMO. The applied product or a metabolite of the applied product may also be non-herbicidal. In one embodiment, an application rate to a field is used from about 0.0025 pounds per Acre (lb/A) to about 9 lb/A, including about 0.25 lb/A to about 1.5 lb/A of dicamba, including, for example, from about 0.25 lb/A to about 1 lb/A, from about 0.5 lb/A to about 1.5 lb/A, and from about 0.5 lb/A to about 1 lb/A, as well as lower or higher amounts and all ranges therebetween, such as about 0.005 lb/A, about 0.01 lb/A, about 0.025 lb/A, about 0.05 lb/A, about 0.15 lb/A, about 0.175 lb/A, about 2 lb/A, about 4 lb/A, about 7 lb/A, and about 12 lb/A. In another embodiment, from about 0.0025 lb/A to about 12 lb/A of DCSA is used, including, for example, from about 0.25 lb/A to about 4 lb/A, from about 0.5 lb/A to about 6 lb/A, and from about 4 lb/A to about 12 lb/A, as well as lower or higher amounts and all ranges therebetween, including about 0.005 lb/A, about 0.01 lb/A, about 0.025 lb/A, about 0.05 lb/A, about 0.15 lb/A, about 0.175 lb/A, about 0.25 lb/A, about 0.5 lb/A, about 1 lb/A, about 3 lb/A, about 5 lb/A, about 8 lb/A, about 12 lb/A, about 15 lb/A, and about 20 lb/A. In certain embodiments of the invention, the dicamba or the product of DMO-mediated metabolism may be applied repeatedly, as well as at a non-herbicidal application rate.

In specific embodiments DCSA is provided to a plant, including any part thereof, by applying dicamba to the plant and allowing the metabolism of the plant to produce DCSA. In this way, health benefits can be obtained by direct application of dicamba. Alternatively, DCSA or a different product of the metabolism of dicamba may be administered directly.

A plant used in an embodiment of the invention may comprise a transgene that encodes DMO. The plant may be a dicotyledonous plant. Examples of dicotyledonous plants include alfalfa, beans, beet, broccoli, cabbage, canola, carrot, cauliflower, celery, Chinese cabbage, cotton, cucumber, eggplant, flax, Jerusalem artichoke, lettuce, lupine, melon, pea, pepper, peanut, potato, pumpkin, radish, rapeseed, spinach, soybean, squash, sugarbeet, sunflower, tomato, and watermelon. In certain embodiments, the plant is selected from the group consisting of cotton, canola, or a legume such as soybean or alfalfa. In a particular embodiment, the plant is a soybean plant (*Glycine max*). In another embodiment, the plant is a cotton plant (*Gossypium* sp., such as *G. hirsutum*).

In certain embodiments the plant may be a monocotyledonous plant. Examples of monocotyledonous plants include barley, corn, leek, onion, rice, sorghum, sweet corn, wheat, rye, millet, sugarcane, oat, triticale, switchgrass, and turfgrass. In certain embodiments, the plant may be a cereal (Gramineae), such as corn (*Zea mays*). In a particular embodiment, the plant is corn.

The plant may further be defined as tolerant to a herbicide selected from the group consisting of glyphosate, glufosinate, 2,4-D, isoxaflutole, dicamba, and sulfonylurea, including any combinations thereof, and may be treated with any such herbicides. In certain embodiments, the plant is tolerant to glyphosate and sulfonylurea, or to glufosinate and sulfonylurea. In yet other embodiments, the plant is tolerant to glyphosate and dicamba. In a particular embodiment, the plant is tolerant to dicamba through the presence of a transgene that detoxifies dicamba. In another particular embodiment, the plant does not comprise a transgene that detoxifies dicamba.

In yet another aspect, the invention provides a method for enhancing the yield of a plant comprising contacting the plant with an amount of dicamba, or a product of DMO-mediated metabolism of dicamba, effective to increase the yield of the plant relative to a plant of the same genotype grown under the same conditions but not contacted with the dicamba or a product of DMO-mediated metabolism of dicamba. The plant may be in a crop production field. The method may further comprise contacting a population of plants with the dicamba or a product of DMO-mediated metabolism thereof. The product of DMO-mediated metabolism may be 3,6-DCSA, 3,5-DCSA, or 3-CSA, or a metabolite of 3,6-DCSA, 3,5-DCSA, or 3-CSA, such as DCGA (5-OH DCSA; DC-gentisic acid).

In specific embodiments of the method, the plant may contain a transgene that encodes DMO. The plant may be, for example, a dicotyledonous or monocotyledonous plant as set forth herein. The plant may further be defined as tolerant to a herbicide selected from the group consisting of glyphosate, glufosinate, 2,4-D, mesotrione, thiazopyr, isoxaflutole, bromoxynil, atrazine, fluazifop-P, and sulfonylureas/imidazolinones, including any combination thereof, and may be treated with any such herbicides.

Another embodiment of the invention comprises a method for improving the health of a seed, comprising contacting the seed with dicamba or a product of DMO-mediated metabolism thereof in an amount that improves the health of the seed as compared to a seed of the same genotype not contacted with the dicamba or product of DMO-mediated metabolism thereof.

In still yet another aspect, the invention provides a method of producing 3,6-DCSA comprising contacting a population of plants in a crop production field with dicamba, wherein the plants comprise a transgene encoding DMO.

In yet another aspect, the invention provides a method for improving the health of a plant exposed to a heavy metal, comprising contacting the plant with DCSA in combination with the heavy metal or prior to the heavy metal application or with dicamba or a product of DMO-mediated metabolism thereof in an amount that improves the health of the heavy metal treated plant as compared to a plant of the same genotype not contacted with DCSA, dicamba or product of DMO-mediated metabolism thereof.

Another embodiment of the invention comprises a method for improving the health of a plant treated with or exposed to AMPA, comprising contacting the plant with DCSA in combination with glyphosate or prior to the glyphosate treatment to a glyphosate tolerant plant or application of dicamba or a product of DMO-mediated metabolism thereof in an amount that improves the health of the glyphosate treated glyphosate tolerant plant as compared to a plant of the same genotype not contacted with DCSA, dicamba or product of DMO-mediated metabolism thereof.

In still yet another aspect, the invention provides a method for increasing the germination rate of a seed, comprising contacting the seed with dicamba or a product of DMO-mediated metabolism thereof in an amount that improves the germination of the seed as compared to a seed of the same genotype not contacted with the dicamba or a product of DMO-mediated metabolism thereof. In one embodiment, the seed may be in a crop production field. In another embodiment, the method may further comprise contacting a population of seeds with the dicamba or a product of DMO-mediated metabolism thereof. In a particular embodiment, the seed may be coated with a composition comprising the dicamba or a product of DMO-mediated metabolism thereof. The product of DMO-mediated metabolism, in one embodiment of the invention, may be one or more of 3,6-DCSA, 3,5-DCSA, or 3-CSA, or a metabolite of 3,6-DCSA, 3,5-DCSA, or 3-CSA. In another embodiment, the product may be an analog of DCSA. In a certain embodiment, the dicamba or a product of DMO-mediated metabolism dicamba may be herbicidal and the plant may comprise a transgene that encodes DMO. The dicamba or a product of DMO-mediated metabolism dicamba may, in another embodiment, may be non-herbicidal.

In one embodiment, the seed is treated with about 0.1 grams to about 100 grams of dicamba or a product of DMO-mediated metabolism, including for example, from about 0.1 grams to about 95 grams, about 0.1 grams to about 50 grams, about 0.1 grams to about 105 grams, about 0.1 grams to about 150 grams, about 0.05 grams to about 100 grams, about 0.5 grams to about 100 grams, as well as lower or higher amounts and all ranges therebetween, including about 0.001 grams, about 0.005 grams, about 0.01 grams, about 0.025 grams, about 0.05 grams, about 0.075 grams, about 0.125 grams, about 0.15 grams, about 0.175 grams, about 1.0 grams, about 3.0 grams, about 5.0 grams, about 10 grams, about 25 grams, about 75 grams, about 90 grams, about 99, grams, about 101 grams about 110 grams, about 125 grams, per about 100 kilograms of seed, or amounts thereabout, for example, about 50 kilograms, about 75 kilograms, about 80 kilograms, about 0 kilograms, about 95 kilograms, about 96 kilograms, about 97 kilograms, about 98 kilograms, about 99 kilograms, about 101 kilograms, about 102 kilograms, about 103 kilograms, about 104 kilograms, about 105 kilograms, about 110 kilograms, about 120 kilograms, about 125 kilograms, and about 150 kilograms.

In a specific embodiment, the seed may be from a dicotyledonous plant, for example alfalfa, beans, beet, broccoli, cabbage, carrot, cauliflower, celery, Chinese cabbage, cotton, cucumber, eggplant, flax, lettuce, lupine, melon, pea, pepper, peanut, potato, pumpkin, radish, rapeseed, spinach, soybean, squash, sugarbeet, sunflower, tomato, and watermelon. In another embodiment, the seed may be from a monocotyledonous plant, for example, barley, corn, leek, onion, rice, sorghum, sweet corn, wheat, rye, millet, sugarcane, oat, triticale, switchgrass, and turfgrass. In one embodiment, the seed may be a seed of a plant tolerant to a herbicide selected from the group consisting of glyphosate, glufosinate, 2,4-D, mesotrione, dithiopyr, isoxaflutole, bromoxynil, atrazine, fluazifop-P, and sulfonylureas/imidazolinones. In yet another embodiment, the seed may be contacted with at least one herbicide, for example glyphosate, glufosinate, 2,4-D, mesotrione, thiazopyr, isoxaflutole, bromoxynil, atrazine, fluazifop-P, and sulfonylureas/imidazolinones.

In still yet another aspect, the invention provides a method for reducing or preventing yellow flash in a plant, comprising contacting the plant with dicamba or a product of DMO-mediated metabolism thereof in an amount that reduces or prevents the yellow flash. In one embodiment, the invention further comprises identifying the plant as exhibiting yellow flash or at risk of exhibiting yellow flash prior to contacting the plant with dicamba or a product of DMO-mediated metabolism. The plant may be in a crop production field. In another embodiment, a population of plants may be contacted with the dicamba or a product of DMO-mediated metabolism thereof. In specific embodiments, the product of DMO-mediated metabolism is 3,6-DCSA, 3,5-DCSA, or 3-CSA, or a metabolite of 3,6-DCSA, 3,5-DCSA, or 3-CSA, and in another embodiment, it is an analog of DCSA. The product of DMO-mediated metabolism of dicamba may be herbicidal and the plant may comprise a transgene that encodes DMO, in another embodiment, the product is not herbicidal.

In yet another embodiment, the plant comprises a transgene conferring glyphosate tolerance. The plant may, in one embodiment, be contacted with a tank mix comprising glyphosate and the dicamba or a product of DMO-mediated metabolism thereof and the glyphosate may be present in an amount that would damage the plant in the absence of the dicamba or a product of DMO-mediated metabolism thereof.

In one embodiment the plant may a dicotyledonous plant, such as alfalfa, beans, beet, broccoli, cabbage, carrot, cauliflower, celery, Chinese cabbage, cotton, cucumber, eggplant, flax, lettuce, lupine, melon, pea, pepper, peanut, potato, pumpkin, radish, rapeseed, spinach, soybean, squash, sugarbeet, sunflower, tomato, and watermelon. In another embodiment, the plant is a monocotyledonous plant, such as barley, corn, leek, onion, rice, sorghum, sweet corn, wheat, rye, millet, sugarcane, oat, triticale, switchgrass, and turfgrass. The plant, in one embodiment, may be tolerant to a herbicide, such as glyphosate, glufosinate, 2,4-D, mesotrione, dithiopyr, isoxaflutole, bromoxynil, atrazine, fluazifop-P, and sulfonylureas/imidazolinones and in another embodiment may be contacted with at least one herbicide, for example glyphosate, glufosinate, 2,4-D, mesotrione, thiazopyr, isoxaflutole, bromoxynil, atrazine, fluazifop-P, and sulfonylureas/imidazolinones.

In still yet another aspect, the invention provides a method for reducing or preventing the deleterious health effect of a heavy metal or heavy metal salt on a plant, comprising contacting the plant with dicamba or a product of DMO-mediated metabolism thereof in an amount that reduces or prevents the deleterious health effect of exposure of the plant to the heavy metal or heavy metal salt. In one embodiment, the dicamba or a product of DMO-mediated metabolism thereof to the plant in a composition that comprises the heavy metal or heavy metal salt. In a further embodiment, the composition comprises an active including, for example, a fungicide, a herbicide, a nematicide and an insecticide.

In one embodiment, the invention further comprises the step of identifying the plant as being exposed to the heavy metal or heavy metal salt or at risk for exposure to the heavy metal or heavy metal salt. The plant may be in a crop production field. In a certain embodiment, the heavy metal may be selected from the group consisting of copper, iron, aluminum, lead, mercury, cadmium, manganese, nickel, and zinc. In specific embodiments, the product of DMO-mediated metabolism is 3,6-DCSA, 3,5-DCSA, or 3-CSA, or a metabolite of 3,6-DCSA, 3,5-DCSA, or 3-CSA, the product may also be an analog of DCSA. The product may further be herbicidal and the plant may comprise a transgene that encodes DMO, or the product may not be herbicidal.

A plant used in one embodiment may be a dicotyledonous plant. Examples of dicotyledonous plants include, for example, alfalfa, beans, beet, broccoli, cabbage, carrot, cauliflower, celery, Chinese cabbage, cotton, cucumber, eggplant, flax, lettuce, lupine, melon, pea, pepper, peanut, potato, pumpkin, radish, rapeseed, spinach, soybean, squash, sugarbeet, sunflower, tomato, and watermelon. In another embodiment, the plant may be a monocotyledonous plant. Examples of monocotyledonous plants include, for example, barley, corn, leek, onion, rice, sorghum, sweet corn, wheat, rye, millet, sugarcane, oat, triticale, switchgrass, and turfgrass.

In another embodiment the plant may be tolerant to a herbicide, for example glyphosate, glufosinate, 2,4-D, mesotrione, dithiopyr, isoxaflutole, bromoxynil, atrazine, fluazifop-P, and sulfonylureas/imidazolinones and may be contacted with at least one herbicide, for example glyphosate, glufosinate, 2,4-D, mesotrione, thiazopyr, isoxaflutole, bromoxynil, atrazine, fluazifop-P, and sulfonylureas/imidazolinones.

In still yet another aspect, the invention provides a method for producing doubled haploid plant tissue comprising the steps of a) obtaining a haploid plant tissue; b) treating the haploid plant tissue with a chromosome doubling agent; and c) contacting the haploid plant tissue or a doubled haploid tissue obtained therefrom prior to, concurrently with or subsequent to step b) with a composition comprising dicamba, a product of DMO-mediated metabolism thereof, acetyl salicylic acid, salicylic acid or combinations thereof, in an amount that increases the efficiency with which doubled haploid tissue is obtained relative to a haploid tissue treated with the same conditions without said composition. In specific embodiments, the chromosome doubling agent may be for instance nitrous oxide gas, an anti-microtubule herbicide, an anti-microtubule agent, and a mitotic inhibitor or may further be amiprophosmethyl (APM), pronamide, oryzalin, trifluralin, colchicine, griseofulvin, taxanes, paclitaxel, docetaxel, vinca alkaloids, vinblastine, vincristine, and vinorelbine. In another embodiment, the product of DMO-mediated metabolism may be 3,6-DCSA, 3,5-DCSA, or 3-CSA, or a metabolite of 3,6-DCSA, 3,5-DCSA, or 3-CSA.

DETAILED DESCRIPTION OF THE INVENTION

Figure 7:
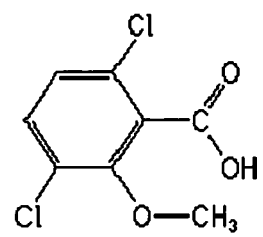
FIG. 7 chemical structures of dicamba and 3,6-DCSA.
Figure 7:
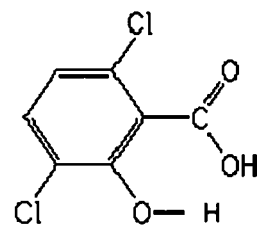

In accordance with the invention, methods are provided for improving plant health, including increasing disease resistance of a plant, conferring enhanced tolerance to oxidative stress on a plant, and/or enhancing the yield of a plant. The plant health and other benefits of providing dicamba, or a metabolite of dicamba such as 3,6-DCSA, or DCGA (5-OH DCSA; DC-gentisic acid) are particularly surprising given that dicamba is normally highly toxic to many plant species. "Dicamba" refers to 3,6-dichloro-o-anisic acid or 3,6-dichloro-2-methoxy benzoic acid (FIG. 7) and its acids and salts. Its salts include isopropylamine, diglycoamine, dimethylamine, potassium and sodium. Examples of commercial formulations of dicamba include, without limitation, Banvel™ (as DMA salt), Clarity® (as DGA salt, BASF), VEL-58-CS-11™ and Vanquish™ (as DGA salt, BASF).

The invention therefore relates, in one aspect, to the surprising discovery that treatment with dicamba to a dicamba resistant plant, comprising a dicamba monooxygenase (DMO) transgene, confers improved health to the plant. Such health benefits may include, for example, resistance to biotic and abiotic stresses to the plant. In specific embodiments, dicamba, 3,6-DCSA (see, e.g., FIG. 7), and analogs thereof may be used to obtain one or more health benefit selected from disease resistance, oxidative stress resistance, and yield. In further embodiments, such treatments may induce a plant response generally termed "Systemic acquired resistance" ("SAR").

Dicamba, 3,6-DCSA, DCGA, and other products of DMO-mediated metabolism of dicamba, and substrates of DMO may thus induce improvements in plant health. A "product of DMO-mediated metabolism of dicamba" may include 3,6-DCSA, a product of metabolism of 3,6-DCSA, or an analog thereof. Proteins produced in response to application of dicamba or DCSA may have a direct antimicrobial activity (e.g. a pathogenesis-related protein such as chitinase), or may have another function that potentiates one or more of improved plant health, disease resistance, oxidative stress resistance, and enhanced yield. Thus, one aspect of the invention is a method of producing 3,6-DCSA or DCGA comprising contacting a population of plants in a crop or production field with dicamba. The plants may be transgenic plants comprising a DMO transgene.

In certain aspects of the invention, a plant may be contacted with a product of in planta DMO-mediated metabolism of dicamba, such as 3,6-DCSA, or DCGA, such that the plant displays enhanced stress resistance as compared to an otherwise identical plant that has not been contacted with dicamba or a product of DMO-mediated metabolism of dicamba.

In one embodiment, the plant may be defined as lacking a DMO transgene and contacted with a non-herbicidal product of DMO-mediated metabolism of dicamba, such as 3,6-DCSA. It was found, for example, that cotton plants contacted with 3,6-DCSA survive inoculation with the plant pathogenic oomycete *Pythium ultimum* that under the same conditions kills otherwise identical plants grown under the same conditions but not contacted with 3,6-DCSA.

In another aspect, a plant may be contacted with dicamba, 3,6-DCSA, DCGA, and/or other products of DMO-mediated metabolism in planta, which yields increased tolerance to oxidative stress. Such stress may be environmental or, for instance, be caused by the presence of an herbicide, pathogen, or other agent such as ozone. In one embodiment, the tolerance to oxidative stress is enhanced such that the plant's photosynthetic activity is not decreased, or is less affected, by the presence of the oxidative stress. Photosynthetic activity may be assayed by means well known in the art, for instance, by measuring electron transfer through photosystems I and/or II (e.g. Peterson and Arntzen, 1982; Allen and Holmes, 1986). In another embodiment, the growth, development, flowering, or yield of the plant is not deleteriously affected, or is less affected, by the presence of an oxidative stress if the plant has been contacted with dicamba, 3,6-DCSA, or another product of DMO-mediated metabolism of dicamba. In yet another embodiment, the necrotizing effect of oxidative stress is reduced.

In specific embodiments of the invention, a plant treated in accordance with the invention may be defined as growing in a crop production field. By "crop production field" is meant a growing environment in which a crop plant is typically grown in a field for production purposes, including seed production, rather than a laboratory greenhouse. In further embodiments of the invention, a population of plants may be defined as growing in a crop production field and treated in accordance with the invention. The plant treated in accordance with the invention may be an immature plant undergoing vegetative growth and sensitive to disease or weed pressure, such as a soybean plant in growth stage VE to V3-V4. The plant may also be at a later growth stage.

The chemical structure of 3,6-DCSA is as follows (I):

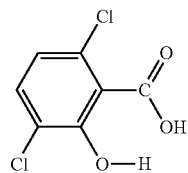

An analog of 3,6-DCSA may be defined, for example, as a substituted benzoic acid, and biologically acceptable salts thereof, wherein substitution on the benzoic acid may include mono-, di-, tri-, or tetra-substitution at the 3-, 4-, 5- and/or 6-positions. Substituents may be chosen for instance from among: lower alkyl groups of 1 to 4 carbons; the halogens fluorine, chlorine, bromine or iodine; an amino group, wherein the nitrogen may carry 0, 1, or 2 identical or different lower alkyl groups of from 1 to 4 carbons each; the nitro group; the formyl group; the acetyl group; the hydroxymethyl group; the methoxycarbonyl group; the hydroxyl group; an alkylthio-, alkylsulfoxy or alkylsulfonyl group, wherein the alkyl group is comprised of from 1 to 4 carbons, or a mono-, di- or trifluoromethyl group. Biologically acceptable salts include those of the common alkali metals sodium and potassium, the alkaline earths magnesium or calcium, zinc, or ammonium or simple alkylammonium cations, such as mono-, di-, tri- or tetramethylammonium cations.

The product of DMO-mediated metabolism may be conjugated to a glucoside which may be hydrolyzed back to the aglycone to modulate, e.g. prolong, the health benefit. In certain embodiments, conjugation to a sugar such as glucose, galactose, or mannose, among others, is contemplated. In other embodiments, conjugation to an amino acid (non-limiting examples of which include alanine, leucine, aspartate, or glutamate) is contemplated.

In still another aspect, the application or presence of dicamba, or 3,6-DCSA, or other product of DMO-mediated metabolism confers enhanced yield to a plant, as compared to the yield of the plant of the same genotype not contacted with dicamba, or 3,6-DCSA, or other product of DMO-mediated metabolism, but grown in the same conditions. In certain embodiments, the plant may be a soybean, cotton, rapeseed, or corn plant, among others.

In another aspect, a plant may be contacted with a non-herbicidal precursor molecule that is converted to a SAR-inducing metabolite within the plant. In certain embodiments, the plant may comprise a DMO transgene, and the resulting encoded DMO may convert the precursor molecule to a SAR-inducing metabolite. In particular embodiments, 2-methoxy, 3,5-dichloro benzoic acid or 2-methoxy, 3-chloro benzoic acid may be applied to a plant and converted by DMO to 3,5-DCSA, or 3-CSA, respectively, to yield any one or more of improved plant health, increased disease resistance of a plant, enhanced tolerance to oxidative stress on a plant, and/or enhancement of the agronomic yield of a plant.

The methods of the invention may be used in connection with, in one embodiment, dicotyledonous (dicot) crop plants. Non-limiting examples of such dicotyledonous plants include alfalfa, beans, beet, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tomato, and watermelon. In some embodiments, the dicot is soybean, cotton, or rapeseed. In other embodiments, the methods of the invention may be used in connection with monocotyledonous crop plants including, but not limited to, barley, corn, leek, onion, rice, sorghum, sweet corn, wheat, rye, millet, sugarcane, oat, triticale, switchgrass, and turfgrass.

Biotic and abiotic crop stress conditions may include, for example, drought, shade, fungal disease, viral disease, bacterial disease, insect infestation, nematode infestation, weed infestation, cold temperature exposure, heat exposure, osmotic stress, oxidative stress, reduced nitrogen nutrient availability, reduced phosphorus nutrient availability and high plant density. Such conditions may be unfavorable for a plant, which adversely affects plant metabolism, growth and/or development.

The methods of the present invention find use in the control, prevention or treatment of a wide variety of plant diseases. The methods of the present invention include prophylactic inhibition and therapeutic treatment of infection by plant pathogens. Plant pathogens can be classified by their life cycle in relation to a plant host, these classifications include, obligate parasites, facultative parasites, and facultative saprophytes. Obligate parasites can only survive and reproduce by obtaining nutrition from living plant cells and are in direct contact with these cells, examples of obligate fungal parasites of plants include, but are not limited to members of Uredinales (rusts), Ustilaginales (smuts and bunts), Erysiphales (powdery mildews), and Oomycetes (water molds and downy mildews), Facultative parasites are organisms that generally survive as saprophytes on the products of other organisms or dead organisms but can become parasitic when the conditions are favorable. Facultative saprophytes are organisms that generally survive as parasites of plants but can survive as saprophytes when a susceptible plant host is not available. The method of the present invention can be used to control, prevent or treat infection from a wide array of plant pathogens that include obligate parasites, facultative parasites, and facultative saprophytes, which include, but are not limited to the following:

Ascomycete fungi such as of the genera *Venturia, Podosphaera, Erysiphe, Manilinia, Mycosphaerella,* and *Uncinula*; Basidiomycete fungi such as from the genera *Hemileia, Rhizoctonia,* and *Puccinia*; Fungi imperfecti such as the genera *Botrytis, Helminthosporium, Rhynchosporium, Fusarium* (i.e., *F. monoliforme*), *Septoria, Cercospora, Aiternaria, Pyricularia, Pseudocercosporella* (i.e., *P. herpotrichoides*), and *Verticillium*; Oomycete fungi such as from the genera *Phytophthora* (i.e., *P. parasitica, P. medicaginis, P. megasperma*), *Peronospora* (i.e, *P. tabacina*), *Bremia, Pythium,* and *Plasmopara*; as well as other fungi such as *Scleropthora macrospora, Sclerophthora rayissiae, Sclerospora graminicola, Peronosclerospora sorghi, Peronosclerospora philippinensis, Peronosclerospora sacchari* and *Peronosclerospora maydis, Physopella zeae, Cercospora zeae-maydis, Colletotrichum graminicola, Gibberella zeae, Exserohilum turcicum, Kabatiella zeae,* and *Bipolaris maydis* may cause disease that is controlled, prevented, or treated by the methods of the present invention. Particularly preferred pathogens include, but are not limited to: *Puccinia, Rhizoctonia,* GGT (*Gaeumannomyces graminis* var. *tritici*), stripe rust, *Phakopsora* sp. including *P. pachyrhizi* (causing Asian soybean rust), *Fusarium* species, *Verticillium* species such as

*V. dahliae, Cercospora zeae-maydis* (causing Gray leaf spot), *Phytophthora* species and Corn rust. Thus, the diseases controlled, prevented or treated include, for example, diseases of alfalfa plants such as root rot (*Phytophora medicaginis, P. megasperma*); rice plant such as Rice blast (*Pyricularia oryzae*), Helminthosporium leaf blight (*Helminthosporium oryzae, Cochliobolus miyabeanus*), Bakanae disease (*Gibberella fujikuroi*), Seedling blight (*Rhizopus oryzae*), Sheath blight (*Rhizoctania solani*), and so on; those of oat such as Crown rust (*Puccinia coronata*), and so on; those of barley such as Powdery mildew (*Erysiphe graminis*), Scald (*Rhynchosporium secalis*), Spot-blotch (*Cochliobolus sativus*), mottleleaf (*Helminthosporium gramineum, Pyrenophora grainineum*), Net blotch (*Pyrenophora teres*), Stinking smut (*Tilletia caries*), Loose smut (*Ustilago nuda*), and so on; those of wheat such as Powdery mildew (*Erysiphe graminis*), Glume-blotch (*Leptosphaeria nodorum, Septoria nodorum*), Stripe rust (*Puccinia striiformis*), Typhula snow blight (*Typhula incarnata*), Eye spot (*Pseudocercosporella herpotrichoides*), Snow mold (*Calonectria graminicola, Fusarium nivale*), Stem rust (*Puccinia graminis*), Black snow blight (*Typhula ishikariensis*), Scab (*Gibberella zeae*), Leaf rust (*Puccinia recondita, Puccinia triticina*), Stripe (*Helminthosporium gramineum*), Stinking smut (*Tilletia caries*), Speckled leaf blight (*Septoria tritici*), Loose smut (*Ustilago tritici*), and so on; those of turfgrass such as Gray leaf spot (*Pyricularia grisea*) and so on; those of corn such as Corn rust, Damping-off (*Pythium debaryanum*), and so on; those of rye such as Purple snow mold (*Fusarium nivale*), and so on; those of cotton such as *Verticillium* wilt (*V. dahliae*), Seedling disease (*Pythium ultinum, Colletototrichum gossypii, Pythium* sp.; *Rhizoctonia solani, Thielaviopsis* sp.), Bacterial blight (*X. campestris* pv. *maivacearum*), and so on; those of potato such as Late blight (*Phytophthora infestans*), and so on; those of tobacco plants such as Downy mildew (*Peronospora tabacina*), Foot rot (*Phytophthora parasitica* var), *Septoria* blight (*Cercospora nicotianae*), and so on; those of sugar beet such as Leaf spot (*Cercospora beticola*), Damping-off (*Pythium debaryanum, Rhizoctonia solani, Pythium aphanidermatum*), and so on; those of paprika such as Gray mold (*Botrytis cinerea*), and so on, those of kidney bean such as Gray mold (*Botrytis cinerea*), Sclerotinia seed rot (sclerotial rot; *Sclerotinia sclerotiorum*), Southern blight (*Corticium rolfsii*), and so on; those of broad bean such as Powdery mildew (*Erysiphe polygoni, Sphaerotheca fuliginea*), Rust (*Uromyces fabae, Uromyces phaseoli*), Gray mold (*Botrytis cinerea*), and so on; those of peanut such as *Ascochyta* spot (*Mycosphaerelia arachidicola*), and so on; those of cabbage such as Damping blight (*Rhizoctonia solani*), and so on; those of cucumber such as Powdery mildew (*Sphaerotheca fuliginea*), Stem rot (*Fusarium oxysporum*), Gummy stem blight (*Mycosphaerella melonis*), Downy mildew (*Pseudoperonospora cubensis*), Gray mold (*Botrytis cinerea*), Sclerotial seed rot (*Sclerotinia sclerotiorum*), Anthracnose (*Colletotrichum lagenarium*), Damping blight (*Fusarium oxysporum, Pythium aphanidermatum, Rhizoctonia solani*), and so on; those of Komatsuna (i.e. *Brassica rapa* var.) such as *Alternaria* sooty spot (*Alternaria brassicicola*), Club root (*Plasmodiophora brassicae*), and so on; those of celery such as Speckled leaf blotch (*Septoria apii*), and so on; those of radish such as Yellows (*Fusarium oxysporum*), and so on, those of tomato such as *Fusarium* wilt (*Fusarium oxysporum*), Foot rot (*Phytophthora infestans*), Ring leaf-spot (*Alternaria solani*), Gray mold (*Botrytis cinerea*), Leaf blight (*Phytophthora capsici*), Black rot (*Alternaria tomato*), and so on; those of eggplant such as Brown rot (*Phytophthora capsici*), vascular wilt pathogens, e.g. *Verticillium* wilt (*Verticillium albo-atrum, V. dahliae*), and so on, those of Chinese cabbage such as Black rot (*Alternaria japonica*), Club root (*Plasmodiophora brassicae*), and so on; those of sweet pepper such as Foot rot (*Phytophthora capsici*), Gray mold (*Botrytis cinerea*), and so on; those of lettuce such as Gray mold (*Botrytis cinerea*), and so on, those of citrus fruits such as Pod and stem blight (*Diaporthe citri*), and so on, those of pear such as Scab (*Venturia nashicola*), Black rot (*Alternaria kikuchiana*), Japanese Pear Rust (*Gymnosporangium hareaenum*). Brown spot (caused by *Stemphylium vesicarium*) and so on; those of grape such as Downy mildew (*Plasmopara viticola*), Gray mold (*Botrytis cinerea*), Sphaceloma scab (*Eisinoë ampelina*), and so on; those of peach such as Leaf curl (*Taphrina deformans*), Scab (*Cladosporium carpophilum*), shot hole (*Mycosphaerella cerasella*), and so on, those of apple such as Powdery mildew (*Podosphaera leucotricha*), Scab (*Venturia inaequalis*), Gray mold (*Botrytis cinerea*), Black rot (*Botryosphaeria obtusa*), Brown spot (*Gymnosporangium yamadae*), White root rot (*Rosellinia necatrix*), *Alternaria* leaf spot (*Alternaria mali*), and so on; and other diseases of grains, fruits and vegetables such as oil-seed rape, sunflower, carrot, pepper, strawberry, melon, kiwi fruit, onion, leek, sweet potato, fig, ume, asparagus, persimmon, soybean, adzukibean, watermelon, crown daisy, spinach, tea and so on.

Viral, bacterial, and nematode-caused diseases, such as viral mosaic diseases (e.g. caused by Tobacco mosaic virus, Soybean mosaic virus, Alfalfa mosaic virus, or Cucumber mosaic virus), soybean dwarf virus, and bean pod mottle virus, among others; those caused by bacteria including *Pseudomonas syringae* pvs., such as *P. syringae* pv. *glycinea, P. syringae* pv. *coronafaciens; Xanthomonas campestris* pvs., such as *X. campestris* pv. *glycines; Xanthomonas oryzae; Xanthomonas translucens; Xanthomonas axonopodis* pv. *malvacearum* (Bacterial blight of cotton); *Erwinia* spp. and including *Pantoea* spp.; and *Clavibacter* spp., among others, are also included, as well as those caused by nematodes such as *Meloidogyne incognita, Pratylenchus penetrans, Xiphinema* sp., and *Heterodera* sp., among others.

In one embodiment of the invention, the biotic crop stress is a rust fungus (Basidiomycete). Some agriculturally important plant rust diseases include, without limitation, those caused by *Puccinia* sp., such as cereal rusts caused by *Puccinia coronata, Puccinia graminis, Puccinia striiformis, Puccinia sorghi, Puccinia polysora*, and *P. recondita*; rusts caused by *Gymnosporangium* sp.; White Pine Blister Rust caused by *Cronartium ribicola*; Coffee Rust caused by *Hemileia vastatrix*; and rust diseases caused by *Uromyces* sp. In a particular embodiment, the crop is soybean and the biotic crop stress is Soybean Rust caused by *Phakopsora* sp.

In certain aspects of the invention, dicamba or 3,6-DCSA may be provided or applied to a plant alone or in combination with another herbicide or other active ingredient. Application of the other herbicide may occur prior to, concurrently, or after application of the dicamba, 3,6-DCSA, or other product of DMO-mediated metabolism of dicamba.

"Application to a plant" may also comprise applying dicamba, 3,6-DCSA, or other product of DMO-mediated metabolism of dicamba, to a seed. "Health" of a seed may be measured, for instance, in terms of percent germination, time to germination, resistance to seedling diseases or stresses, seedling vigor, or by the stand of a resulting crop.

The preparation of such compositions for use in connection with the current invention will be apparent to those of skill in the art in view of the disclosure. These compositions will typically include, in addition to the active ingredient, components such as surfactants, solid or liquid carriers, solvents and binders. Examples of surfactants that may be used for application to plants include the alkali metal, alkaline earth metal or ammonium salts of aromatic sulfonic acids, e.g., ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these. Common practice in the case of surfactant use is about 0.25% to 1.0% by weight, and more commonly about 0.25% to 0.5% by weight.

In one embodiment of the invention, dicamba may be provided in combination with glyphosate. By "in combination with" it is meant that dicamba may be applied concurrently, or prior or after glyphosate. Due to synergism, this embodiment may be used to reduce amounts of either herbicide to achieve the same degree of activity as an application of only one of the herbicides. For example, the invention may involve applying less than a 1× rate of glyphosate and/or dicamba, relative to the standard manufacturer labeled rate. Examples of respective glyphosate and dicamba application rates include, in addition to 1× rates, from about a 0.25×-0.95× of either herbicide, specifically including about 0.5×, 0.6×, 0.7×, 0.8×. 0.85×, 0.9×, and 0.95× of either herbicide and all derivable combinations thereof, as well as higher rates such as 0.97× and 0.99×. In certain plant health embodiments, it may be desirable to use individual applications of dicamba in these amounts. Alternatively, 1× and higher application rates may be made in view of the finding that even high application rates of dicamba do not significantly damage plants containing a DMO transgene. The 1× application rates are set by the manufacturer of a commercially available herbicide formulation and are known to those of skill in the art. For example, the label for Fallow Master™, a glyphosate and dicamba mixture having a ratio of glyphosate:dicamba of about 2:1 recommends application rates of about 451 g/ha (311 ae g/ha glyphosate:140 ae g/ha dicamba) to 621 ae g/ha (428 ae g/ha glyphosate: 193 ae g/ha dicamba) depending upon the weed species and weed height. Glyphosate may also be applied in combination with 3,6-DCSA. Beneficial effects on plant health may be obtained by contacting plants or plant parts with dicamba by utilizing dicamba for weed control. Or, a non-herbicidal rate of dicamba may be provided to a crop, which nevertheless results in beneficial health effects.

The dicamba, or 3,6-DCSA, or analog of 3,6-DCSA, or product thereof that can be produced via DMO-mediated metabolism of dicamba, may be applied outside of a typical application window for weed control, by for instance varying the timing of application, the growth stage of the crop and/or weed plants, or the application rate, according to the knowledge of one of skill in the art. The plant identified as in need of improved health may be an immature plant undergoing vegetative growth and sensitive to a disease or to weed growth, such as a soybean plant in growth stage VE to V3 or V4. The soybean plant may also be at a post-V4 growth stage. The plant may also be a corn plant prior to or during growth stages such as VE to V3, V7, V10, V15, or VT. The corn plant may also be at a post-vegetive growth stage. The plant may also be a cotton plant undergoing vegetative growth such as prior to blooming, including for instance, prior to or during the seedling emergence, first true leaf, first vegetative side shoot, first fruiting branch, or 1$^{st}$ square (fruiting bud) formation growth stages. The cotton plant may also be at a flowering growth stage, or during boll-development. The growth stage of a plant may also be defined by days after planting.

"Dicamba" refers to 3,6-dichloro-o-anisic acid or 3,6-dichloro-2-methoxy benzoic acid and its acids and salts. Its salts include isopropylamine, diglycoamine, dimethylamine, potassium and sodium. Examples of commercial formulations of dicamba include, without limitation, Banvel™ (as DMA salt), Clarity® (as DGA salt), VEL-58-CS-11™ and Vanquish™ (as DGA salt, BASF). "Glyphosate" refers to N-phosphonomethylglycine and salts thereof. Glyphosate is commercially available in numerous formulations. Examples of these formulations of glyphosate include, without limitation, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt, ROUNDUP® WEATHERMAX containing glyphosate as its potassium salt; ROUNDUP® DRY and RIVAL® herbicides, which contain glyphosate as its ammonium salt; ROUNDUP®GEOFORCE, which contains glyphosate as its sodium salt; and TOUCHDOWN® herbicide, which contains glyphosate as its trimethylsulfonium salt.

In certain embodiments, the invention may relate to use of a DMO transgene. In one aspect of the invention, the DMO may be encoded by a nucleic acid sequence selected from the group consisting of: a) a nucleic acid sequence encoding the polypeptide of SEQ ID NO:1; b) a nucleic acid sequence comprising the sequence of SEQ ID NO:2; and c) a nucleic acid sequence encoding a polypeptide with at least 90% sequence identity to the polypeptide of SEQ ID NO:1 wherein the polypeptide has dicamba monooxygenase activity and comprises cysteine at a position corresponding to amino acid 112 of SEQ ID NO:1. In another aspect, the nucleic acid sequence may encode a polypeptide with at least 90% sequence identity to the polypeptide of SEQ ID NO:1 that has dicamba monooxygenase activity and comprises tryptophan at a position corresponding to amino acid 112 of SEQ ID NO:1. In such embodiments, a DNA vector may be provided comprising a DMO-encoding nucleic acid described herein operably linked to a promoter. The promoter may be functional in a plant cell. In certain embodiments, the nucleic acid sequence encoding dicamba monooxygenase may be operably linked to a chloroplast transit peptide (CTP). In other embodiments, the invention may relate to use of a transgene that confers tolerance to glyphosate, such as CP4 EPSPS. A sequence of such a gene may be found, for example, in U.S. Pat. No. RE39,247, herein incorporated by reference.

DMOs having a capability to degrade dicamba, as well as glyphosate- or other herbicide-tolerance genes, can readily be prepared and assayed for activity according to standard methods. Such sequences can also be identified by techniques known in the art, for example, from suitable organisms including bacteria that degrade herbicides (U.S. Pat. No. 5,445,962; Cork and Krueger, 1991; Cork and Khalil, 1995). One means of isolating a DMO or other sequence is by nucleic acid hybridization, for example, to a library constructed from the source organism, or by RT-PCR using mRNA from the source organism and primers based on the disclosed sequences. The invention therefore encompasses use of nucleic acids hybridizing under stringent conditions to a DMO encoding sequence described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed.

Variants can also be chemically synthesized, for example, using the known DMO polynucleotide sequences according to techniques well known in the art. For instance, DNA sequences may be synthesized by phosphoroamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing codons to host-preferred codons. The codon preferences of many host cells are known (PCT WO 97/31115; PCT WO 97/11086; EP 646643; EP 553494; and U.S. Pat. Nos. 5,689,052; 5,567,862; 5,567,600; 5,552,299 and 5,017,692). The codon preferences of other host cells can be deduced by methods known in the art. Also, using chemical synthesis, the sequence of the DNA molecule or its encoded protein can be readily changed to, for example, optimize expression (for example, eliminate mRNA secondary structures that interfere with transcription or translation), add unique restriction sites at convenient points, and delete protease cleavage sites.

Modification and changes may be made to the polypeptide sequence of a protein such as the DMO sequences provided herein while retaining enzymatic activity. The following is a discussion based upon changing the amino acids of a protein to create an equivalent, or even an improved, modified polypeptide and corresponding coding sequences. It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the DMO peptide sequences described herein or other herbicide tolerance polypeptides and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine.

A DNA construct comprising a CTP sequence operably linked to a DMO sequence can be expressed in test system such as protoplasts, transiently or stably transformed plant cells by operably linked them to a promoter functional in plants. Examples describing such promoters include U.S. Pat. No. 6,437,217 (maize RS81 promoter), U.S. Pat. No. 5,641,876 (rice actin promoter; OsAct1), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,388,170 (e.g. PC1SV promoter), the PC1SV promoter of SEQ ID NO:41, U.S. Pat. No. 6,635,806 (gamma-coixin promoter), and U.S. Pat. No. 7,151,204 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), and the chlorophyll a/b binding protein gene promoter, etc. In the present invention, CaMV35S with enhancer sequences (e35S; U.S. Pat. Nos. 5,322,938; 5,352,605; 5,359,142; and 5,530,196), FMV35S (U.S. Pat. Nos. 6,051,753; 5,378,619), peanut chlorotic streak caulimovirus (PC1SV; U.S. Pat. No. 5,850,019), At.Act 7 (Accession #U27811), At.ANT1 (US Patent Application 20060236420), FMV.35S-EF1a (US Patent Application 20050022261), eIF4A10 (Accession #X79008) and AGRtu.nos (GenBank Accession V00087; Depicker et al, 1982; Bevan et al., 1983), rice cytosolic triose phosphate isomerase (OsTPI; U.S. Pat. No. 7,132,528), and rice actin 15 gene (OsAct15; U.S. Patent Application 2006-0162010) promoters may be of particular benefit.

A 5' UTR that functions as a translation leader sequence is a DNA genetic element located between the promoter sequence of a gene and the coding sequence may be included between a promoter and CTP-DMO sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362,865), AtAnt1, TEV (Carrington and Freed, 1990), and AGRtunos (GenBank Accession V00087; Bevan et al., 1983) among others. (Turner and Foster, 1995). In the present invention, 5' UTRs that may in particular find benefit are GmHsp (U.S. Pat. No. 5,659,122), PhDnaK (U.S. Pat. No. 5,362,865), AtAnt1, TEV (Carrington and Freed, 1990), OsAct1 (U.S. Pat. No. 5,641,876), OsTPI (U.S. Pat. No. 7,132,528), OsAct15 (U.S. Publication No. 20060162010), and AGRtunos (GenBank Accession V00087; Bevan et al., 1983).

The 3' non-translated sequence, 3' transcription termination region, or poly adenylation region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. These sequences may be included downstream of a CTP-DMO sequence. An example of a 3' transcription termination region is the nopaline synthase 3' region (nos 3'; Fraley et al., 1983). The use of different 3' nontranslated regions is exemplified (Ingelbrecht et al., 1989). Polyadenylation molecules from a *Pisum sativum* RbcS2 gene (Ps.RbcS2-E9; Coruzzi et al., 1984), AGRtu.nos (Genbank Accession E01312), E6 (Accession #U30508), and TaHsp17 (wheat low molecular weight heat shock protein gene; Accession #X13431) in particular may be of benefit for use with the invention.

In addition to expression elements described above, an intron may be required in between a promoter and a 3' UTR for expressing a coding region, especially in monocots. An "intron" refers to a polynucleotide molecule that may be isolated or identified from the intervening sequence of a genomic copy of a gene and may be defined generally as a region spliced out during mRNA processing prior to translation. Alternately, introns may be synthetically produced. Introns may themselves contain sub-elements such as cis-elements or enhancer domains that effect the transcription of operably linked genes. A "plant intron" is a native or non-native intron that is functional in plant cells. A plant intron may be used as a regulatory element for modulating expression of an operably linked gene or genes. A polynucleotide molecule sequence in a transformation construct may comprise introns. The introns may be heterologous with respect to the transcribable polynucleotide molecule sequence. Examples of introns include the corn actin intron (U.S. Pat. No. 5,641,876), the corn HSP70 intron (ZmHSP70; U.S. Pat. No. 5,859,347; U.S. Pat. No. 5,424,412), and rice TPI intron (OsTPI; U.S. Pat. No. 7,132,528) and are of benefit in practicing this invention.

Any of the techniques known in the art for introduction of transgene constructs into plants may be used in accordance with the invention (see, for example, Mild et al., 1993). Suitable methods for transformation of plants are believed to include virtually any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184. Through the application of techniques such as these, the cells of virtually any plant species may be stably transformed, and these cells may be developed into transgenic plants. Techniques that may be particularly useful in the context of cotton transformation are disclosed in U.S. Pat. Nos. 5,846,797, 5,159,135, 5,004,863, and 6,624,344. Techniques for transforming *Brassica* plants in particular are disclosed, for example, in U.S. Pat. No. 5,750,871; and techniques for transforming soybean are disclosed in, for example, Zhang et al., 1999, U.S. Pat. Nos. 6,384,301, and 7,002,058. Techniques for transforming corn are disclosed, for instance, in WO9506722. Some non-limiting examples of plants that may find use with the invention include alfalfa, barley, beans, beet, broccoli, cabbage, carrot, canola, cauliflower, celery, Chinese cabbage, corn, cotton, cucumber, dry bean, eggplant, fennel, garden beans, gourd, leek, lettuce, melon, oat, okra, onion, pea, pepper, pumpkin, peanut, potato, pumpkin, radish, rice, sorghum, soybean, spinach, squash, sweet corn, sugarbeet, sunflower, switchgrass, tomato, watermelon, and wheat.

After effecting delivery of exogenous DNA to recipient cells, the next steps in generating transgenic plants generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. Any suitable plant tissue culture media, for example, MS or N6 media (Murashige and Skoog, 1962; Chu et al., 1975); may be modified by including further substances such as growth regulators. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to shoot formation. Cultures are transferred periodically until sufficient shoot formation had occurred. Once shoot are formed, they are transferred to media conducive to root formation. Once sufficient roots are formed, plants can be transferred to soil for further growth and maturity.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Unmodified and modified protein molecules and their corresponding nucleic acid molecules providing tolerance to one or more herbicides are well known in the art. For example:

a) sequences encoding tolerance to glyphosate include 5-enolpyruvylshikimate-3-phosphate synthases (EPSPS; U.S. Pat. Nos. 5,627,061, U.S. Pat. No. RE39,247, U.S. Pat. Nos. 6,040,497, 5,094,945, WO04074443, and WO04009761), glyphosate oxidoreductase (GOX; U.S. Pat. No. 5,463,175), glyphosate decarboxylase (WO05003362 and U.S. Patent Application 20040177399), and glyphosate-N-acetyl transferase (GAT; U.S. Patent publication 20030083480) conferring tolerance to glyphosate;

b) dicamba monooxygenase (DMO, encoded by ddmC) conferring tolerance to auxin-like herbicides such as dicamba (U.S. Patent Application publications 20030115626, 20030135879; Wang et al., 1996; Herman et al., 2005);

c) phosphinothricin acetyltransferase (bar) conferring tolerance to phosphinothricin or glufosinate (U.S. Pat. Nos. 5,646,024, 5,561,236, EP 275,957; U.S. Pat. Nos. 5,276,268; 5,637,489; 5,273,894);

d) 2,2-dichloropropionic acid dehalogenase conferring tolerance to 2,2-dichloropropionic acid (Dalapon) (WO9927116);

e) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366, 4,761,373; 5,633,437; 6,613,963; 5,013,659; 5,141,870; 5,378,824; 5,605,011);

f) haloarylnitrilase (Bxn) for conferring tolerance to bromoxynil (WO8704181A1; U.S. Pat. No. 4,810,648; WO8900193A);

g) modified acetyl-coenzyme A carboxylase for conferring tolerance to cyclohexanedione (sethoxydim) and aryloxyphenoxypropionate (haloxyfop) (U.S. Pat. No. 6,414,222);

h) dihydropteroate synthase (sulI) for conferring tolerance to sulfonamide herbicides (U.S. Pat. Nos. 5,597,717; 5,633, 444; 5,719,046);

i) 32 Id) photosystem II polypeptide (psbA) for conferring tolerance to triazine herbicides (Hirschberg et al., 1983);

j) anthranilate synthase for conferring tolerance to 5-methyltryptophan (U.S. Pat. No. 4,581,847);

k) dihydrodipicolinic acid synthase (dapA) for conferring to tolerance to aminoethyl cysteine (WO8911789);

l) phytoene desaturase (crtI) for conferring tolerance to pyridazinone herbicides such as norflurazon (JP06343473);

m) hydroxy-phenyl pyruvate dioxygenase for conferring tolerance to cyclopropylisoxazole herbicides such as isoxaflutole (WO 9638567; U.S. Pat. No. 6,268,549);

n) modified protoporphyrinogen oxidase I (protox) for conferring tolerance to protoporphyrinogen oxidase inhibitors (U.S. Pat. No. 5,939,602); and o) aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluoroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Production of Transgenic Soybean Containing a DMO Gene

Transgenic soybean plants comprising a DMO-encoding transgene were obtained by *Agrobacterium*-mediated transformation of soybean tissue from cultivars Thorne, NE3001, and A3525, using standard procedures (e.g. U.S. Pat. Nos. 6,384,301, 7,002,058 or Zhang et al., 1999) with a binary vector containing a DMO-encoding polynucleotide which encodes the polypeptide of SEQ ID NO:1.

Example 2

Induction of a Pathogen Related Protein Involved in Disease Resistance by Dicamba and DCSA Transgenic and control soybean seeds (cultivars Thorne, NE3001, A3525) were planted into 3.5-inch square plastic pots containing Redi-earth™ (Scotts-Sierra Horticultural Products Co., Marysville, Ohio). The pots were placed on capillary matting in 35 inch×60 inch fiberglass watering trays for overhead and/or sub-irrigation for the duration of the test period so as to maintain optimum soil moisture for plant growth and were fertilized with Osmocote® (14-14-14 slow release; Scotts-Sierra Horticultural Products Co., Marysville, Ohio) at the rate of 100 gm/cu.ft. to sustain plant growth for the duration of greenhouse trials.

The plants were grown in greenhouses at 29°/21° C. day/night temperature with relative humidity between 15%-50% to simulate warm season growing conditions of late spring. A 14 hour minimum photoperiod was provided with supplemental light at about 600 µE (micro-Einsteins) as needed. Trials were established in a randomized block design randomized by rate with 4 to 6 replications of each treatment.

All herbicide applications were made with the track sprayer using a Teejet® 9501E flat fan nozzle (Spraying Systems Co, Wheaton, Ill.) with air pressure set at a minimum of 24 psi (pounds per square inch), or 165 kpa (kilopascals)). The spray nozzle was kept at a height of about 16 inches above the top of plant material for spraying. The spray volume was 10 gallons per acre or 93 liters per hectare. Applications were made when plants had reached V-3 stage.

Events carrying a DMO transgene in their genome were grown and treated with dicamba (Clarity®, BASF) at 1 lb/Acre at Post-V3 stage. Leaf samples were harvested after 0, 3, 8, 24, 48, 72 hrs after treatment (HAT) and frozen for further analysis. In another experiment, DMO-containing plants were sprayed with either dicamba or DCSA at 0.25, 0.5 and 1 lb/Acre rate and tissue samples were collected 24 HAT. RNA was extracted and analyzed by northern blot analysis using PR-2, i.e., β-1,3-glucanase as a probe. PR-2 is a pathogenesis-related protein known to degrade fungal membranes and thus provide protection against fungal pathogens (U.S. Pat. No. 5,670,706 and Uknes et al., 1992).

Tissue samples were ground in Falcon™ tubes (BD Biosciences, Franklin Lakes, N.J.) with liquid nitrogen and glass/metal beads. Sub-samples were taken in Eppendorf tubes. A plant RNA mini kit was used for extracting RNA following manufacturer protocol (Qiagen, Valencia, Calif.). RNA concentration was estimated using measurement of OD at 260 and 280 nm. Five µg (micrograms) of RNA was precipitated by adding 1/10 volume of 3M sodium acetate and 2.5 volume of 100% ethanol and storing the tubes at −20° C. for 48 hrs. The tubes were centrifuged for 20 min at 4° C. and supernatant was discarded. Seventy percent ethanol was added to the tubes and RNA was resuspended in it gently. The tubes were then centrifuged for 3.5 minutes, and the RNA pellet was dried for about 30 to 60 min and resuspended in 15 µl of loading buffer (Gel loading buffer II from Ambion, Austin, Tex.) by brief vortexing and mixing.

RNA samples and RNA markers (RNA ladder; Invitrogen, Carlsbad, Calif.) were denatured at 65° C. for 10 min and kept on ice until loaded in gel made from 1% agarose and 2% formaldehyde in 1×MOPS buffer. The gel was run at 17 V for 16 h in 1×MOPS buffer and stained with ethidium bromide to visualize RNA samples and markers in the gel. The gel was washed for 30 min in water to remove ethidium bromide followed by two washes in 20×SSC (NaCl and sodium citrate) for 15 min each.

RNA samples and markers were blotted on the membrane (Nytran® PLUS, Midwest Scientific, Valley Park, Mo.) using a rapid downward transfer system (Turblotter™ and blotting stack, Whatman-Schleicher & Schuell; Florham Park, N.J.) for 5-6 hours. The membrane was rinsed with water, U.V. cross linked and placed on a paper to dry. The membrane was pre-hybridized in warm 15 ml DIG Easy Hyb buffer (Roche, Penzberg, Germany) at 50° C. for 30 min. PR-2 probe was labeled with DIG and synthesized using PCR DIG probe synthesis kit according to manufacturer's instructions (Roche) and boiled for 5 minutes and cooled on ice before adding to warm 15 µl DIG Easy Hyb buffer. Hybridization was done overnight at 50° C. The RNA blot was washed at high stringency twice, for 5 min and 15 min, in 2×SSC and 0.1% SDS solution at room temperature. Two more washes followed for 30 min each in 0.5×SSC and 0.1% SDS solution at 68° C. The blot was then washed in 1× washing buffer (Roche) for 2 min and blocked using a blocking reagent (Roche) for 30 min to 3 hours at room temperature with moderate shaking. The blot was transferred to 30 ml DIG antibody solution (75 mU/ml, Roche) for 30 min Unbound antibodies were removed by 3 washes of 15 min each with 1× washing buffer. The blot was equilibrated in 1× detection buffer (Roche) for 3 min. Ready to use CDP-STAR (disodium 2-chloro-5-(4-methoxyspiro {1,2-dioxetane-3,2'-(5'-chloro) tricyclo[3.3.1.1$^{3,7}$]decan}-4-yl)-1-phenyl phosphate; Roche) was added to the blot placed in a detection bag. The bag was sealed and blot was exposed to BIOMAX film (Kodak) for 1.5 hours.

Figure 1:
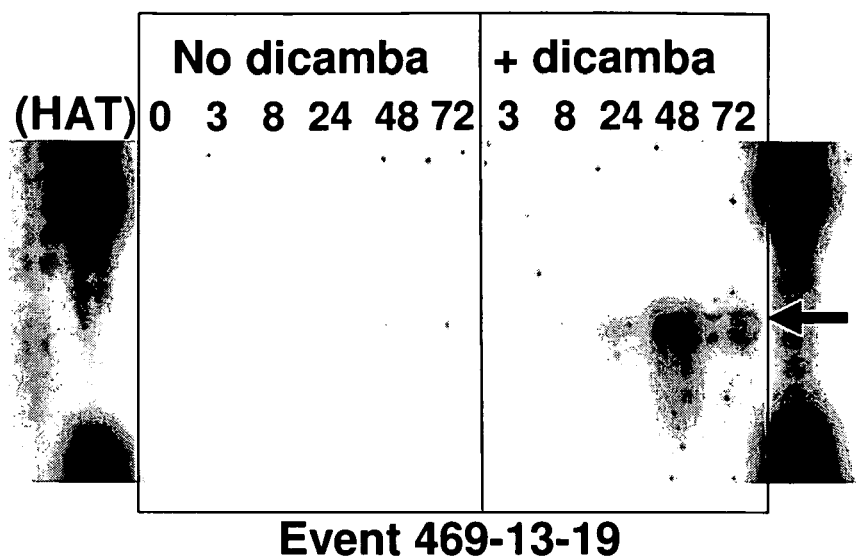
FIG. 1 induction of PR2 at various time points after treating DMO plants with dicamba.

FIG. 1 shows induction of PR2 at various time points after treating with dicamba. The peak induction was at 48 hrs. There was no induction of PR2 in plants not treated with dicamba.

Figure 2:
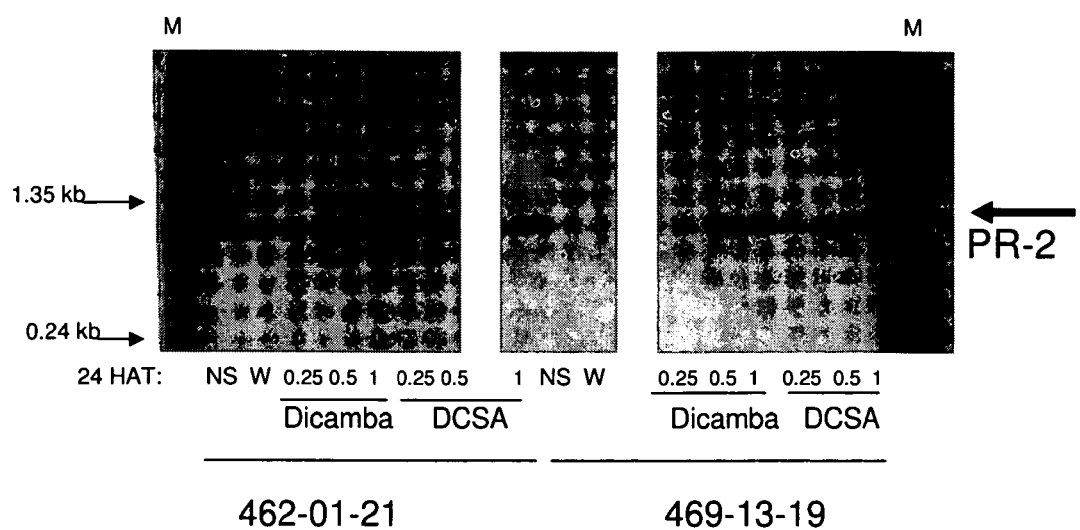
FIG. 2 induction of PR2 at various rates of dicamba and DCSA 24 hrs after treatment in two independent transgenic lines of soybean.

FIG. 2 shows induction of PR2 at various rates of dicamba and DCSA 24 hrs after treatment in two independent transgenic lines of soybean. There was no induction of PR2 in plants not treated with dicamba or DCSA or treated with water only.

Induction of PR5 by dicamba or DCSA was also observed using a probe specific to PR5 (Uknes et al., 1992) and experimental procedures as described above for PR2.

Example 3

DCSA Provides Fungal Disease Resistance

Figure 3:
FIG. 3 effect of treating cotton plants with *Pythium ultimum*, in the presence or absence of 3,6-DCSA.

Ten-day old Roundup Ready® Flex Cotton (Event MON 88913; U.S. Publ. 20060059590) seedlings were sprayed with a mixture of Roundup Weather Max® (Monsanto Company, St. Louis, Mo.) and 3,6-DCSA (BASF). The control plants were sprayed with water only. The cotton seedlings from both treatments were inoculated with *Pythium ultimum* by dipping seedling into inoculum slurry, 24 hours after the spray application. The positive control plants were neither sprayed nor inoculated with *P. ultimum*. As shown in FIG. 3, the cotton seedlings inoculated with *P. ultimum* but that did not receive application of a mixture of Roundup Weather Max® (Monsanto Company, St. Louis, Mo.) and 3,6-DCSA died as a result of *P. ultimum* infection within 10 days after inoculation. However, infection by *P. ultimum* was not established in the plants that received a mixture of Roundup Weather Max® (Monsanto Company, St. Louis, Mo.) and 3,6-DCSA. Cotton plants treated with Roundup® and DCSA were as healthy as were the plants not inoculated with *P. ultimum*. The results indicate that the combined treatment of Roundup Ultra Max and DCSA reduced *P. ultimum* infection when plants were inoculated with *Pythium* 24 hours after the treatment with DCSA.

Example 4

DCSA Provides Bacterial Disease Resistance

Figure 4:
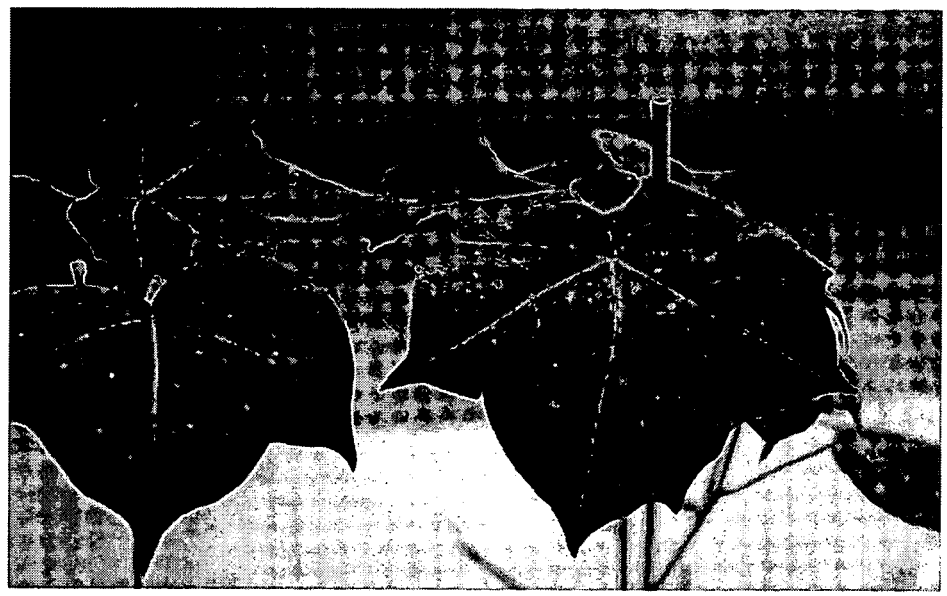
FIG. 4 effect of treating cotton plants with *Xanthomonas campestris* pv. *malvacearum* in the presence or absence of 3,6-DCSA.

In this example, two-week old cotton plants were sprayed with DCSA while control plants received spray application of water only. The plants were inoculated with bacterial blight pathogen (*Xanthomonas campestris* pv. *malvacearum*) about 24 hours after the DCSA spray application using a tooth pick inoculation method. As shown in the FIG. 4, the cotton plants inoculated with the bacterial pathogen but not sprayed with DCSA developed necrotic spots, typical symptoms of bacterial blight. However, the cotton plants that received DCSA application 24 hours before inoculation with bacterial pathogen showed only localized lesions (HR response) and no increase in bacterial blight symptoms. The results of this experiment indicate that DCSA application reduced bacterial infection on cotton plants when inoculated with bacterial pathogen 24 hours after the DCSA spray.

Example 5

Dicamba or DCSA Increases Tolerance to Oxidative Stress in Soybean

For this example, the plants were grown as described in the above example. Transgenic and non transgenic soybean plants carrying the DMO gene in their genome were either treated with Paraquat (Gramoxone®; Syngenta) to create oxidative stress or with dicamba followed by Paraquat at V3 stage. The dicamba rate was 1 lb/Acre or 1120 g ae/ha. Paraquat was applied at 30, 70, or 200 g ae/ha. Plants were then evaluated for paraquat injury by visually assessing injury at a particular day after treatment (DAT) for injury on a scale of 0 to 100 percent relative to untreated control plants, with zero representing "no" injury and 100% representing "complete" injury or death. Data were collected and analyzed using suitable statistical methods.

Table 1 shows that significantly reduced Paraquat injury was seen 4 DAT at all three application rates tested on soybean plants carrying DMO gene and treated with dicamba 24 hrs before applying Paraquat.

TABLE 1

Percentage injury to non-transgenic or transgenic soybean plants treated with paraquat or dicamba followed by paraquat at V-3 stage. The % injury was represented as ANOVA mean comparisons (with respect to paraquat treatment). Similar letters represent no statistical difference at the p = 0.05 level.

| | | Paraquat (g ae/ha) | | |
|---|---|---|---|---|
| Plant | Treatment | 30 g | 70 g | 200 g |
| N3001 | Paraquat | 32.5 a | 50.8 a | 75 a |
| DMO-soy 462 | Paraquat | 33.3 a | 48.3 a | 74.2 a |
| DMO-soy 462 | Dicamba f/b Paraquat | 16.7 b | 26.7 b | 51.7 b |
| DMO-soy 469 | Paraquat | 30.8 a | 49.2 a | 76.7 a |
| DMO-soy 469 | Dicamba f/b Paraquat | 15 b | 29.2 b | 50 b |
| | LSD | 6 | 6.7 | 6.3 |

In another experiment, the effect of externally applied DCSA was tested for its benefit in protecting soybean plants from oxidative stress injury caused by Paraquat. Different amounts of DCSA were applied 24 hrs before applying Paraquat to test any correlation between the amount of DCSA applied and the extent of protection obtained from oxidative stress measured in terms of reduction in % injury as described above. Different levels of dicamba were also applied separately to test the same hypothesis.

Table 2 shows, for example, that the application of either dicamba or DSCA provided protection against oxidative stress caused by subsequently applying paraquat. Transgenic plants contacted with Paraquat alone exhibited an injury rate of about 75% whereas transgenic plants contacted with different rates of dicamba or DSCA followed by Paraquat surprisingly showed reduction in injury. Further, the reduction in injury increased with increasing application rate of either dicamba or DCSA. The plants used in this experiment were transgenic. The effect of dicamba is due to in planta conversion of dicamba into DCSA or subsequent metabolism, whereas the effect of DCSA is due to DCSA itself or due to its metabolites.

TABLE 2

Percentage injury to transgenic soybean plants treated with paraquat only, or with dicamba or DCSA followed by paraquat at V-3 stage. The % injury was represented as ANOVA mean comparisons.

| | | | % injury at 5 DAT at different rates of Dicamba or DCSA followed by 100 g ae/ha of paraquat | | |
|---|---|---|---|---|---|
| Transgenic Event | Treatment | % injury at 5 DAT Paraquat alone control 100 g ae/ha | 280 g/ha | 561 g/ha | 1120 g/ha |
| 462-1-21 | Dicamba | 75.83 | 65.00 | 54.17 | 45.83 |
| 462-1-21 | DCSA | 75.83 | 66.67 | 53.33 | 49.17 |
| 469-13-19 | Dicamba | 77.50 | 51.67 | 45.83 | 40.83 |
| 469-13-19 | DCSA | 77.50 | 50.83 | 48.33 | 43.33 |

Example 6

DCSA Increases Tolerance to Oxidative Stress in Cotton

Four different cotton cultivars as indicated in Table 3 were grown in 4-inch pots for two weeks. These cotton plants were either sprayed with DCSA (BASF) at the 1 lb/A rate, or unsprayed (no DCSA application, as control). Experimental plants (treated with DCSA and untreated) were sprayed with Paraquat (Gramoxone®; Syngenta) at 30 gm/ha, 70 gm/ha, and 100 gm/ha rates, 24 hours after the application of DCSA, to simulate oxidative stress. The positive control plants did not receive any chemical treatment (neither DCSA nor Gramoxone® application). All plants were then evaluated for paraquat injury by visual assessment two days after the treatment (DAT) with Gramoxone® on a scale of 0 to 100 percent relative to untreated control plants, with zero representing "no" injury and 100% representing "complete" injury or death of the plant. The same experiment was repeated at two different growth stages of cotton (2 nodes stage and 5 nodes stage).

The results of these experiments shown in Table 3 indicate that Gramoxone® injury was reduced significantly when four varieties of RR cotton were pretreated with DCSA (24 hours) at two different growth stages (two nodes stage and 5 nodes stage). Reduction of injury symptoms was not dependent on the two cotton growth stages tested. Similar results were obtained with non-transgenic cotton cultivar ST474.

TABLE 3

Percentage injury to indicated cotton plant varieties treated with paraquat or DCSA followed by paraquat.

| UNTREATED CONTROL | ST4646B2RF 0 | ST3273B2RF 0 | ST4575BR 0 | ST6622RF 0 |
|---|---|---|---|---|
| Gramoxone ® (30 g a.i./ha) | 31.5 | 35 | 37.5 | 42.5 |
| DCSA (1 lb/Acre) + Gramoxone ® (30 g a.i./ha) | 8.5 | 6 | 12.5 | 7.5 |
| Gramoxone ® (70 g a.i./ha) | 42.5 | 50 | 42.5 | 50 |
| DCSA (1 lb/Acre) + Gramoxone ® (70 g a.i./ha) | 20 | 32.5 | 30 | 35 |
| Gramoxone ® (100 g a.i./ha) | 70 | 50 | 65 | 70 |
| DCSA (1 lb/Acre) + Gramoxone ® (100 g a.i./ha) | 45 | 45 | 40 | 50 |

Example 7

Enhancing Yield by Application of Dicamba to Plants

The yield enhancing-benefit of DSCA was tested by growing non-transgenic and transgenic plants and applying dicamba to transgenic plants and harvesting the seeds. Non-transgenic and transgenic soybean seeds were planted near the beginning of the growing season in several locations at the time of best possible growth conditions such as soil moisture, temperature, and seeding depth. Across all locations seeds were planted under split-plot design with dicamba treatments as whole-plot effects and events as split-plot effects. The design details were as follows: 6 locations, 2 replications/location, 2 rows/plot, row length 12 feet (+3 ft alley), 9 seeds/foot, 108 seeds/row, 5 events (events 1-4 and a fifth event that was segregating); and 4 treatments as shown below in Table 4. In all, 240 plots were planted at 6 locations (40 per location).

TABLE 4

Details of four dicamba treatments applied on transgenic soybean.

| Treatment | 1st Application | | 2nd Application | |
|---|---|---|---|---|
| | Dicamba Rate | Plant Stage | Dicamba Rate | Plant Stage |
| 1 | 0 | N/A | 0 | N/A |
| 2 | 1.5 lb ae/Acre | Preemergence (Pre) | 0 | N/A |
| 3 | 0 | N/A | 1.5 lb ae/Acre | Postemergence (Post; V3-4) |
| 4 | 1.5 lb ae/Acre | Preemergence (Pre) | 1.5 lb ae/Acre | Postemergence (Post; V3-4) |

Four non-transgenic border rows were planted all around the trial using a known commercial line such as A3525. Optimum production and management practices known in the art were followed. Maximum pest control and disease control was practiced as needed to prevent confounding effects of dicamba applications. The field was irrigated as needed according to standard practices.

Figure 5:
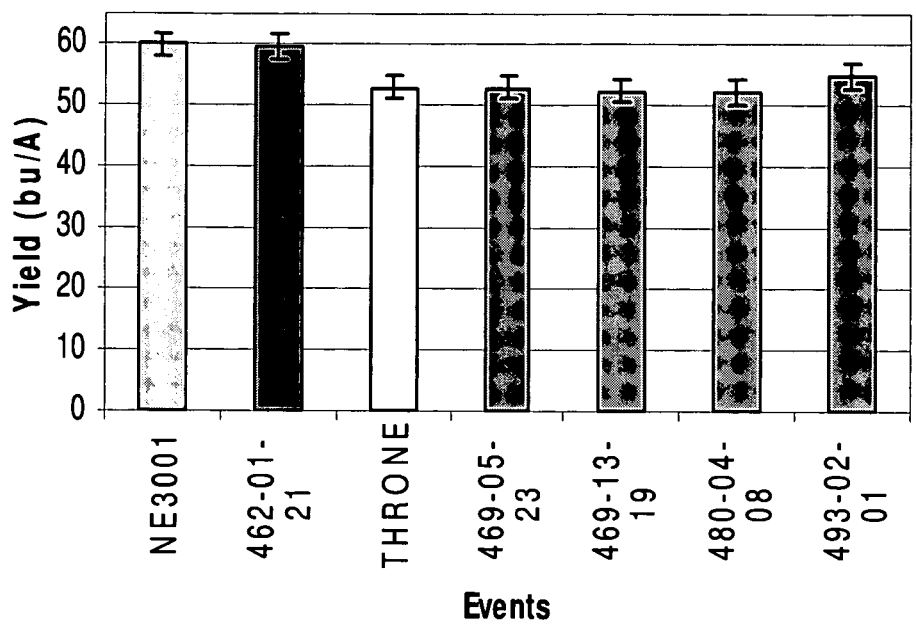
FIG. 5 lack of adverse effect on yield and other agronomic traits of providing a DMO gene in soybean.
Figure 6:
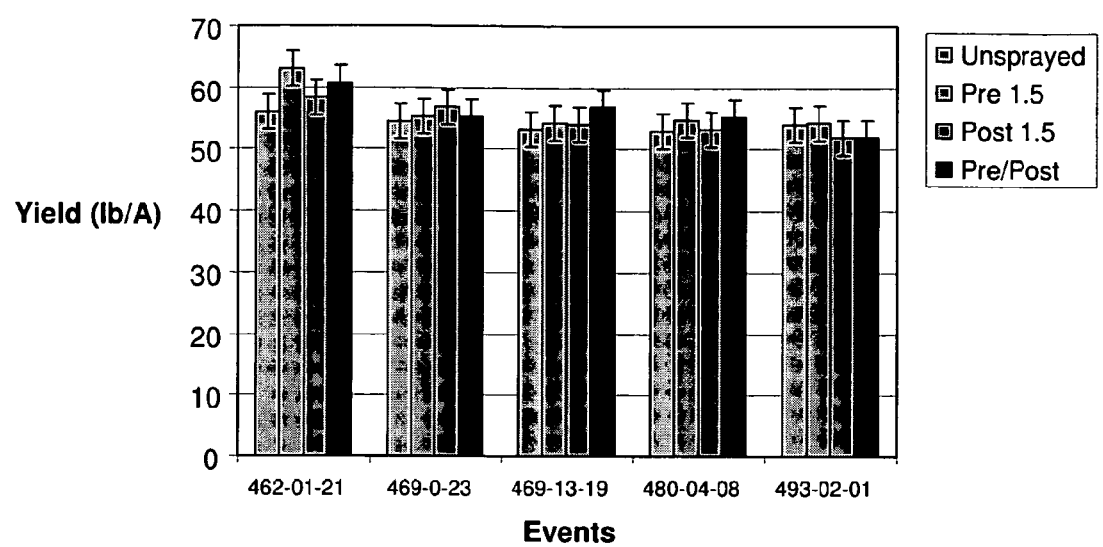
FIG. 6 dicamba spray effect on yield.

Results shown in FIG. 5 indicate that the presence of the DMO transgene confers no yield penalty or other agronomic effects in soybean in the absence of dicamba treatment. Agronomic and efficacy trials also demonstrated no delay in maturity of transgenic plants when compared with control line A3525, nor in dicamba treated plants when compared with untreated plant. In contrast, as shown in FIG. 6, in 4/5 events and 13/15 treatments, dicamba spray showed an increase or equivalent yield to unsprayed controls indicating a yield benefit due to improved plant health by DCSA produced in vivo by the action of DMO on dicamba.

Figure 8:
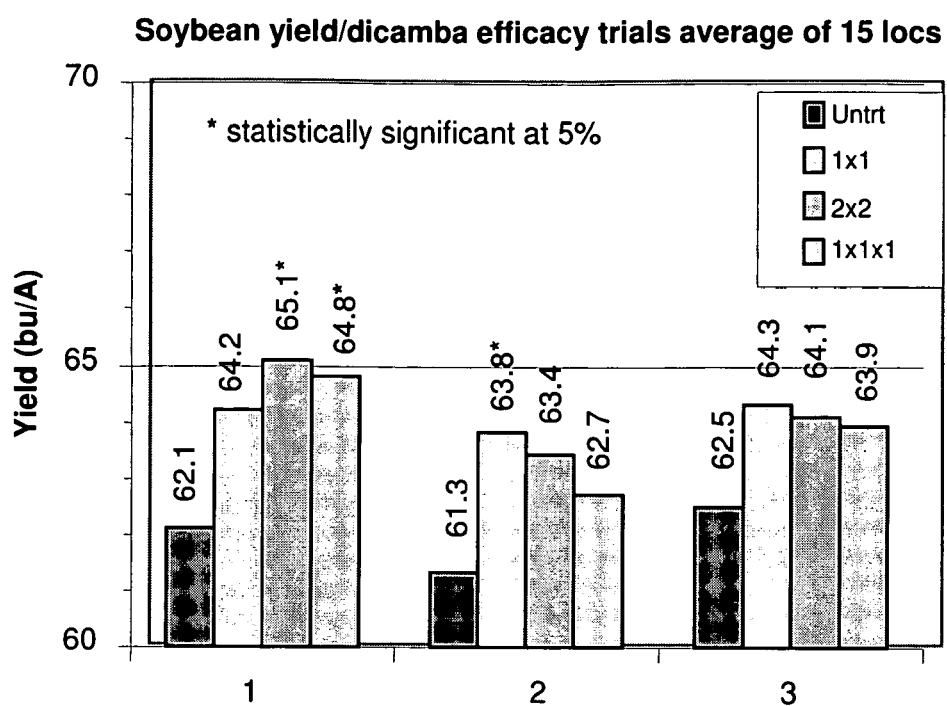
FIG. 8. soybean yield/dicamba efficacy trials average of 15 locations.

In the following year, transgenic soybean events comprising the DMO transgene were field tested for yield (bu/A) in 15 locations (locs) and the results averaged across the 15 locations are shown in FIG. 8. The treatments were: untreated (Untrt); 1 lb/A dicamba at planting followed by 1 lb/A dicamba at V3 growth stage (1×1); 2 lb/A dicamba at planting followed by 2 lb/A dicamba at V3 growth stage (2×2); and 1 lb/A dicamba at planting followed by 1 lb/A dicamba at V3 growth stage followed by 1 lb/A dicamba at R1 stage (1×1×1). Yield increases were observed at all dicamba treatments for the three events tested that ranged from 1.4 to 3 bu/A or up to about 4.6 percent increase in seed yield and statistically significant (5 percent confidence level, SAS 9.1) yield was measured for treatments for events 1 and 2. In another aspect of the invention, treatment with 0.5 lb/A dicamba at planting followed by 0.5 lb/A at V3 growth stage may increase yield.

Example 8

Provision of Multiple Benefits by Expressing Dicamba and Glyphosate Tolerance Genes and Treating Plants with Glyphosate and Dicamba A glyphosate tolerance gene such as CP4 EPSPS has been found to provide glyphosate tolerance and improve plant health by providing resistance against several pathogens, including *Phakopsora pachyrizi* and *Phakopsora meibomiae*, the causal agents of soybean rust, which is provided by direct action of glyphosate on such pathogenic fungi (WO05102057). In the present case, it was shown that DMO provides dicamba tolerance and improves plant health by reducing pathogen and oxidative stresses. Further benefits can be obtained by combining the two genes in a single plant by molecular and breeding methods and treating the plants with glyphosate and dicamba. This will increase the number of options available to growers depending on their market and environmental needs.

Example 9

Control of Cotton Root Knot Nematode (RKN; *Meloidogyne incognita*) by DCSA

DCSA was unexpectedly found to control RKN gall formation, improve plant height and reduce number of eggs produced by the nematode in cotton plants (ST474) (Table 5). Ten to fourteen days old cotton plants were treated with DCSA at the rate of 1 lb/A, 24 hrs before inoculating them with RKN eggs. Cotton plants which were treated with DCSA exhibited no or low gall formation (0.6 vs 2.6), improved plant height (19.8 cm vs 16.9 cm), and reduced egg count (4575 vs 6425) as compared to plants which were not treated with DSCA. Plant height, gall rating, and egg counts were measured 45 days after inoculation. The gall rating scale was 0-5 with 0=no visible galling and 5=heavy galling.

TABLE 5

Control of RKN by DCSA application in cotton.

| | RKN alone | | | RKN + DCSA | | | Un-inoculated Control | | |
|---|---|---|---|---|---|---|---|---|---|
| Plant | Plant Height (cm) | Egg Count/ pot | RKN Gall Rating (0-5) | Plant Height (cm) | Egg Count/ pot | RKN Gall Rating (0-5) | Plant Height (cm) | Egg Count | RKN Gall Rating (0-5) |
| 1 | 15.9 | 2,160 | 2 | 25.4 | 8,160 | 0 | 21.0 | 0.0 | 0.0 |
| 2 | 20.3 | 5,120 | 2 | 25.4 | 9,120 | 0 | 18.4 | 0.0 | 0.0 |
| 3 | 12.1 | 9,480 | 3 | 25.4 | 5,200 | 0 | 19.7 | 0.0 | 0.0 |
| 4 | 20.3 | 5,600 | 3 | 22.2 | 3,720 | 2 | 20.3 | 0.0 | 0.0 |
| 5 | 15.2 | 2,800 | 3 | 17.8 | 3,360 | 1 | 14.0 | 0.0 | 0.0 |
| 6 | 15.2 | 15,400 | 2 | 14.0 | 3,040 | 1 | | | |
| 7 | 20.6 | 7,680 | 3 | 15.9 | 1,800 | 0 | | | |
| 8 | 15.2 | 3,160 | 3 | 12.7 | 2,200 | 1 | | | |
| Mean | 16.9 | 6,425 | 2.6 | 19.8 | 4,575 | 0.6 | 18.7 | 0.0 | 0.0 |
| SE | 1.1 | 1,557 | 0.2 | 1.9 | 962 | 0.3 | 1.0 | 0.0 | 0.0 |

The present invention contemplates that plant disease caused by other plant parasitic nematodes can be reduced by treatment of plant in need of protection from nematode disease with DCSA or treatment of DMO transgenic plants with dicamba.

Example 10

DCSA Provides Protection Against *Verticillium*

DCSA was unexpectedly found to provide protection to cotton plants against *Verticillium dahliae*, causal agent of cotton wilt disease (Table 6). Cotton plants of the variety ST6611, BOLLGARD 2, ROUNDUP READY FLEX, were inoculated with a moderate isolate (DPL) or a virulent isolate (King) of *Verticillium* by a seedling dipping method. Seedlings at the first true leaf stage were taken out from the pots, one inch of roots were cut off, seedlings were dipped in a spore slurry for one minute, and then transplanted back in the pots. These strains were isolated and provided by Dr. Terry Wheeler (Texas A&M University, TX USA). DCSA was applied at the rate of 1 lb/A and glyphosate (ROUNDUP WEATHERMAX, Monsanto Company, St. Louis, Mo.) at the rate of 0.75 lb/A 24 hours before inoculation. Protection against *Verticillium* was measured on a disease severity scale of 1-9:1 being healthy and 9 being dead because of disease, and also was measured as the number of plants that survived out of 10 inoculated plants. Application of DCSA provided protection against both moderate and strong isolates of *Verticillium dahliae*. Inoculated cotton plants that were treated with DCSA showed lower rating and higher survival rating compared to inoculated checks that were not treated with DCSA.

TABLE 6

Control of *Verticillium* by DCSA application to cotton.

| | *Verticillium* (isolate DPL) | | | *Verticillium* (isolate King) | |
|---|---|---|---|---|---|
| Treatment(s) | Severity rating (1-9) | Plant survival rating (out of 10) | Treatment(s) | Severity rating (1-9) | Plant survival rating (out of 10) |
| None | 1 | 10 | None | 1 | 10 |
| Inoculated check | 5 | 8 | Inoculated check | 9 | 0 |
| Glyphosate | 2 | 10 | Glyphosate | 3.5 | 10 |
| DCSA | 1 | 10 | DCSA | 2 | 10 |
| DCSA + glyphosate | 2 | 10 | DCSA + glyphosate | 3 | 9 |

Example 11

DCSA Provides Tolerance to Ozone in Soybeans

Many plants are sensitive to ozone ($O_3$), soybeans are particularly sensitive to ozone damage and show leaf flecking and chlorosis. Ozone can be produced in the atmosphere by a photochemical process in air polluted environments. Soybean production can be affected by ozone when soybeans are cultivated near urban areas or air pollution from urban areas is distributed to agricultural areas where soybeans are grown. An experiment was conducted to determine if DCSA treatment of soybean plants will provide tolerance to oxidative stress caused by ozone. Soybeans were treated with 0.5 lbs/A DCSA approximately 72 hours before exposure to ozone. Controls had no DCSA treatment. Four plants were treated with ozone in one 72 quart sterilite container with a clear plexiglass lid. Ozone was generated at 2 concentrations in the container with the plants at a low rate (2.8 ppm, parts per million) or a high rate (770 ppm) and the plants exposed for 10 hours at these concentrations. Light levels at plant height were ~400μ Einsteins m-2 s-1, enough to insure photosynthesis. Air in the container was mixed using a small fan to insure proper exposure. Plants were removed from the treatment container and placed in a growth chamber to observe symptom development.

The results of the test were that no symptoms were observed at the low exposure rate on the control or DCSA treated plants. Ozone visibly damaged the lower leaves of control plants at the high ozone level showing typical chlorosis and leaf flecking. The DCSA treated plants did not show any lower leaf damage at the high ozone level indicating that DCSA protected the plants from ozone damage.

In an aspect of the present invention, an ozone tolerance benefit is provided due to improved plant health by DCSA applied to a plant in need of ozone tolerance or DCSA produced in vivo by the action of DMO on dicamba in transgenic plants comprising a DMO transgene. It is a further aspect of the invention that treatment of DMO containing transgenic plants with dicamba will enhance the ozone tolerance of the treated plants.

Example 12

DCSA Provides Enhanced Seed Germination

Rapid seed germination is an important agronomic trait that reduces crop losses due to seed rot especially under cool wet conditions. Soybeans seeds of three varieties were germinated in a solution of 1, 10, or 100 µM DCSA or water at normal temperature (22° C.) or cool temperature (15° C.) and rated for seed germination at 1DAT (1 day after treatment) and 2DAT (2 days after treatment) at 22° C. or 4DAT (days after treatment) at 15° C. The germination rate was scored as 1—low, 2—moderate, 3—high for each treatment, 3+—exceptionally high, N=8. The results shown in Table 7 demonstrate that 1-100 µM DCSA stimulates soybean seed germination at both normal and cool temperatures.

Wheat seed (spring wheat variety) was germinated in a solution of 0.1, 1, 10, 100, or 1000 µM DCSA or water at 22° C. and rated 2 DAT for germination using the same rating scale as used for soybean. The results shown in Table 8 demonstrate that wheat seed germination is enhanced in the presence of 10-1000 µM DCSA.

In one aspect of the invention, it is contemplated that seed treated with DCSA or dicamba treated seed of DMO transgenic plants will have enhanced seed germination under normal and adverse environmental conditions.

TABLE 7

Enhanced DCSA treated soybean seed germination at 22° C. and 15° C.

| Treatments 22° C. and 15° C. | Variety 1 | Variety 2 | Variety 3 |
| --- | --- | --- | --- |
| Water, 1DAT, 22° C. | 1 | 1 | 2 |
| 1 µM DCSA | 1 | 2 | 2 |
| 10 µM DCSA | 1 | 2 | 2 |
| 100 µM DCSA | 3 | 3 | 1 |
| Water, 2DAT, 22° C. | 2 | 2 | 2 |
| 1 µM DCSA | 3 | 3 | 2 |
| 10 µM DCSA | 3 | 3 | 3 |
| 100 µM DCSA | 3+ | 3+ | 3 |
| Water, 4 DAT, 15° C. | 1 | 1 | 2 |
| 1 µM DCSA | 1 | 3 | 3 |
| 10 µM DCSA | 3 | 3 | 2 |
| 100 µM DCSA | 3 | 3 | 1 |

TABLE 8

Enhanced DCSA treated wheat seed germination at 22° C.

| Treatments, 22° C., 2DAT | Germination rating |
| --- | --- |
| Water | 1 |
| 0.1 µM DCSA | 1 |
| 1 µM DCSA | 1 |
| 10 µM DCSA | 3 |
| 100 µM DCSA | 2 |
| 1000 µM DCSA | 3 |

Example 13

DCSA Provides Enhanced Drought Tolerance

Drought tolerance is an important agronomic trait. It was found that soybean plants treated with DCSA showed greater tolerance to drought conditions than the same variety not treated with DCSA. Soybean seeds of two varieties (1 and 2) were planted in soil in 4.5 inch pots, 3 seeds per pot. The seeds were germinated and plants grown to the V1 or V2 growth stage. DCSA was prepared (0.36 grams/60 milliliters in 20 percent acetone with 10 percent surfactant) and the plants sprayed with the DCSA solution at a rate equal to 0.5 pounds/Acre (lb/A) or 1.0 (lb/A) at day 0 or day 3 of the experiment. Water was withheld at day 0. The plants were rated on a scale of 1-4 for drought symptoms; 1—no symptoms; 2—minor symptoms, leaf curling and wilting; 3—substantial symptoms and wilting; 4—dead. The treatments were surfactant only, 0.5 lb/A DCSA, and 1.0 lb/A DCSA. The plants were treated with a surfactant or a DCSA solution, water withheld, and drought symptoms rated 2 days after treatment (2DAT), 3 days after treatment (3DAT), and 3DAT after rehydration (water added to soil saturation and plant recovery from drought symptoms measured). Fresh leaf weight (leaf grams fresh weight, leaf gfwt), fresh root weight (root grams fresh weight, root gfwt), leaf dry weight (leaf grams dry weight, leaf gdwt), and root dry weight (root grams dry weight, root gdwt) were measured.

The average drought rating results are shown in Table 9. These results demonstrate that DCSA treated plants of variety 2 showed reduced drought symptoms relative to the control (surfactant treated). The DCSA treated plants of variety 2 with the reduced drought symptoms also showed greater leaf fresh weight, greater root fresh weight and greater root dry weight as shown in Table 10.

In one aspect of the present invention, a drought tolerance benefit is provided due to improved plant health by DCSA applied to a plant in need of drought tolerance or DCSA produced in vivo by the action of DMO on dicamba in transgenic plants comprising a DMO transgene. It is a further aspect of the invention to apply dicamba to DMO containing transgenic plants to enhance drought tolerance.

TABLE 9

Enhanced drought tolerance of DCSA treated soybean plants

| Data collection | Treatment | Variety 1 | Variety 2 |
| --- | --- | --- | --- |
| 2DAT | surfactant | 2 | 1.5 |
| 2DAT | 0.5 lb/A DCSA | 2.25 | 1 |
| 2DAT | 1.0 lb/A DCSA | 1.75 | 1.25 |
| 3DAT | surfactant | 3.5 | 3.5 |
| 3DAT | 0.5 lb/A DCSA | 4 | 2.5 |
| 3DAT | 1.0 lb/A DCSA | 3.75 | 2.5 |
| 3DAT fb rehydration | surfactant | 3.25 | 3 |
| 3DAT fb rehydration | 0.5 lb/A DCSA | 3.75 | 2.5 |
| 3DAT fb rehydration | 1.0 lb/A DCSA | 3.5 | 2.5 |

TABLE 10

Enhanced leaf and root weight of DCSA treated plants under drought stress of variety 2

| Treatments | Leaf gfwt | Root gfwt | Leaf gdwt | Root gdwt |
|---|---|---|---|---|
| surfactant | 8.01 | 12.88 | 2.37 | 1.16 |
| 0.5 lb/A DCSA | 9.45 | 13.74 | 1.43 | 1.25 |
| 1.0 lb/A DCSA | 13.94 | 15.40 | 2.20 | 1.34 |

Example 14

Enhanced Tolerance to Salt or Osmotic Stress

Transgenic soybean seeds containing the DMO gene were germinated in the presence of 100 or 200 mM sodium chloride (NaCl, salt). The seeds had been treated with 0.5 g or 2.5 g of dicamba per 100 kg of seeds. A diglycoamine salt of dicamba (Clarity) was applied to 113.5 g samples of soy in a water based slurry that contained an agricultural dye. Slurry and dye rates were 8 and 0.5 fl oz/cwt. Aliquots of each dicamba solution were added to seeds contained in a glass jar and agitated. After uniform coverage was attained, seeds were placed on towels and allowed to dry. Non-DMO soybeans were treated at rates of 0, 0.5, 2.5, and 5.0 g ai/100 kg. DMO soybeans were treated with 0, 0.5 and 2.5 g ai/100 kg. Seed germination was scored DAT (2 days after treatment) or 5DAT (days after treatment) at 22° C. The germination rate was scored as 1—low, 2—moderate, 3—high for each treatment, N=10.

The dicamba treated soybean seeds that are the progeny of DMO transgenic plants showed enhanced germination in the presence of salt relative to untreated seeds (Table 11). Additionally, a similar analysis can be conducted by treating plants with dicamba or DCSA and measuring plant health in the presence of NaCl. Transgenic soybean plants containing the DMO gene or nontransgenic soybean plants are grown to about V1 growth stage in a growth chamber and treated with a foliar application of surfactant containing an equivalent of 0.5 lb/A of DCSA, 0.5 lb/A of dicamba or a surfactant containing an equivalent of 1.0 lb/A of DCSA or 1.0 lb/A of dicamba or surfactant alone. After the treatment, the plants are subjected to osmotic stress by watering with a solution containing 100 or 200 mM NaCl. The treated plants are measured for tolerance to osmotic stress by rating the stress response.

It is an aspect of the invention that seed treated with DCSA or dicamba treated seeds of DMO transgenic plants will have enhanced seed germination under normal and adverse osmotic environmental conditions and plants treated with DCSA or dicamba treated DMO transgenic plants will have enhanced tolerance to salt or osmotic stress environmental conditions. In another aspect of the invention, DCSA or dicamba treated transgenic seeds or plants will have a enhanced cold/freeze tolerance.

TABLE 11

Enhanced seed germination of DMO transgenic soybean seed treated with dicamba.

| Treatments, 22° C., 100 mM or 200 mM Nacl | Germination rating 2DAT | Germination rating 5DAT |
|---|---|---|
| 100 mM NaCl, 0.0 dicamba | 1 | 2 |
| 100 mM NaCl, 0.5 g ai/100 kg dicamba | 2 | 3 |
| 100 mM NaCl, 2.5 g ai/100 kg dicamba | 2 | 3 |
| 200 mM NaCl, 0.0 dicamba | 1 | 1 |
| 200 mM NaCl, 0.5 g ai/100 kg dicamba | 1.5 | 2 |
| 200 mM NaCl, 2.5 g ai/100 kg dicamba | 1.5 | 1 |

Example 15

DCSA Provides Enhanced Tolerance to Yellow Flash in Soybeans

Yellow flash is a symptom sometimes observed in glyphosate tolerant soybeans treated with glyphosate due to the formation of AMPA (aminomethyl phosphonic acid). A study was conducted to determine if DCSA treatment would protect soybean plants from AMPA induced yellow flash symptoms. Soybean plants were grown to V1-2 growth stage and divided into 3 treatment groups, 3 pots of plants per treatment. The treatments were 0.5 lb/A DCSA, 1.0 lb/A DCSA or surfactant alone. One day after treatment, all of the plants were sprayed with 1 lb/A of AMPA (Sigma Aldrich, St. Louis, Mo.) in surfactant. The plants were observed for yellow flash symptoms eight days after treatment (8DAT) and rated on a scale of 1 (no yellow flash), 2 (moderate yellow flash) and 3 (severe yellow flash). The results, shown in Table 12, demonstrate that DCSA treatment at 1 lb/A DCSA reduced the yellow flash symptom. In an aspect of the present invention, a tolerance to yellow flash is provided due to improved plant health by DCSA applied to a plant in need of yellow flash tolerance or DCSA produced in vivo by the action of DMO on dicamba in transgenic plants comprising a DMO transgene.

TABLE 12

Enhanced tolerance to yellow flash in soybean.

| Treatment | Yellow flash symptoms 8DAT, N = 3 | Average symptoms |
|---|---|---|
| Surfactant alone | 3, 3, 2 | 2.7 |
| 0.5 lb/A DCSA | 3, 3, 3 | 3 |
| 1.0 lb/A DCSA | 1, 2, 2 | 1.7 |

Example 16

2,4-D Tolerance Provided by DMO Transgenic Soybean

Figure 9:
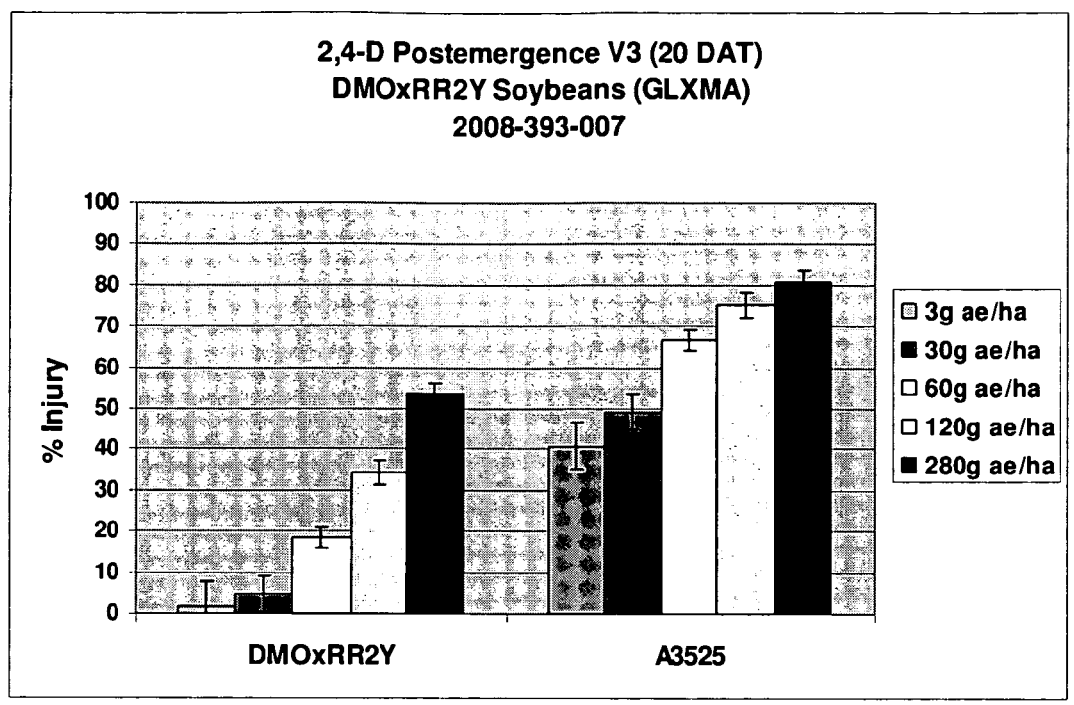
FIG. 9. results of 2,4-D postemergence treatment at V3 on transgenic and non-transgenic soybean plants.

A rate titration of 2,4-D (2,4-D amine, Helena Chemical Co., Memphis, Tenn.) was applied as postemergence (POST) treatment at V3 growth state of breeding stack of DMO soybean and RR2Y (RR2Y is MON89788 event, U.S. application Ser. No. 11/441,914) transgenic soybean. 2,4-D was applied as a postemergence (POST) treatment (V3) at 5 application rates on DMOxRR2Y soybean stack and compared for total crop injury across all application rates. The POST herbicide application rates used for this trial were 3 g ae/ha (acid equivalent/hectare), 30 g ae/ha, 60 g ae/ha, 120 g ae/ha and 280 g ae/ha of 2,4-D. The treated plants were rated for 2,4-D symptoms 20 days after treatment. Shown in FIG. 9, at all application rates, POST 2,4-D injury on the DMOxRR2Y dicamba resistant soybean was significantly (ANOVA test) lower compared to the treated non-transgenic control A3525. In an aspect of the present invention, a DMO transgenic soybean plant shows reduced injury from 2,4-D treatment or accidental exposure to 2,4-D.

Example 17

Enhanced Dihaploid Production

Plant breeding is greatly facilitated by the use of doubled haploid (DH) plants. The production of DH plants enables plant breeders to obtain inbred lines without multigenerational inbreeding, thus decreasing the time required to produce homozygous plants. A great deal of time is spared as homozygous lines are essentially instantly generated, negating the need for multigenerational conventional inbreeding. In particular, because DH plants are entirely homozygous, they are very amenable to quantitative genetics studies. Both additive variance and additive×additive genetic variances can be estimated from DH populations. Other applications include identification of epistasis and linkage effects. Moreover, there is value in testing and evaluating homozygous lines for plant breeding programs. All of the genetic variance is among progeny in a breeding cross, which improves selection gain. Production of DH plants, which entails induction of haploidization followed by diploidization, requires a high input of resources. DH plants rarely occur naturally; therefore, artificial means of production are used. First, one or more lines are generally crossed with an inducer parent to produce haploid seed. The resulting haploid seed, which has a haploid embryo and a normal triploid endosperm, must then undergo doubling.

There are a number of well known approaches known in the art to achieve chromosome doubling. Haploid cells, haploid embryos, haploid seeds, haploid seedlings, or haploid plants can be chemically treated with a doubling agent. Non-limiting examples of known doubling agents include nitrous oxide gas, anti-microtubule herbicides, anti-microtubule agents, colchicine, pronamide, and mitotic inhibitors.

The use of these chemicals during the doubling process is toxic and stressful to the treated plant or seed. In accordance with one embodiment of the invention, salicylic acid and its derivatives are used to pretreatment with salicylic acid or its derivatives can enhance survival rate and chromosome doubling rate of seeds or plant tissues treated with one or more of the doubling agents. To determine quantify the effect of acetyl salicylic acid (ASA) and salicylic acid (SA) on plant health of haploid plants subjected to colchicine treatments, haploid seeds of corn genotype 01DKD2 were treated with 100-500 microMolar (µM) of DCSA, ASA, or SA or combinations thereof by imbibing the seeds in a solution of the compound for 24 hours before colchicine treatment of the seeds. A solution of 0.0625% colchicine (Sigma Aldrich, St. Louis, Mo. Cat#C3915) and 1.5% DMSO (Sigma Aldrich, St. Louis, Mo. Cat#D8779) was used to treat the seeds and the seeds incubated in the solution at 25° C. for 5 days in the dark. The germination rate, survival rate of the treated plants, fertility, and doubling rate were measured. The results shown in Table 13 demonstrate that ASA 250 µM and ASA 100 µM+SA 100 µM enhanced the doubling efficiency of plants recovered from the colchicine treatment.

TABLE 13

ASA and SA treatment of haploid seeds imbibed for 24 hours before colchicine treatment

| Treatment (µM) | Percent germination | 10 inch pot survival | Percent Pollination | Doubling efficiency |
|---|---|---|---|---|
| ASA 100 | 87 | 62 | 86 | 0 |
| ASA 250 | 85 | 60 | 78 | 8 |
| ASA 500 | 68 | 35 | 71 | 5 |
| SA 100 | 80 | 48 | 83 | 2 |
| SA 250 | 85 | 58 | 85 | 3 |
| SA 500 | 85 | 77 | 89 | 3 |
| ASA 100 + SA 100 | 85 | 55 | 76 | 12 |
| ASA 250 + SA 250 | 82 | 62 | 70 | 0 |
| ASA 500 + SA 500 | 85 | 75 | 84 | 3 |
| Water | 90 | 53 | 81 | 5 |

Alternative to seed treatment, plants at the V1-V4 growth stage can be treated with a colchicine solution containing 10-500 µM DCSA, ASA, or SA or combinations thereof as a soil drench or foliar treatment to enhance the doubling efficiency of surviving plants.

In an aspect of the present invention, an enhanced haploid doubling efficiency is provided by treatment with salicylic acid or its analogs, which would include DCSA or DCSA produced in vivo by the action of DMO on dicamba in transgenic plants comprising a DMO transgene.

Example 18

DCSA Provides Enhanced Tolerance to Heavy Metals

Plants are sensitive to heavy metal toxicity. Heavy metals are present in the environment or sometimes applied to plants for pest control. Symptoms of plant injury following treatment with a heavy metal compound, for example, a compound containing copper, are necrotic leaf spotting and flecking with more severe injury resulting in larger reddish brown spots, veinal necrosis and/or necrotic puckered leaves. We tested for the ability of DCSA treatment of soybean plants to reduce the symptoms of copper injury. Soybean seeds were planted in pots in a greenhouse and grown to the V1-2 growth stage. The plants were treated with DCSA and copper sulfate or copper nitrate (Fisher Scientific Co., Pittsburgh, Pa.) There were four foliar spray treatments with 4 replications each: (1) 1000 ppm copper sulfate; (2) DCSA at 0.5 lb/A mixed with a 1000 ppm solution of copper sulfate applied as a tank mix; (3) DCSA at 0.5 lb/A application followed by (fb) 1 hour later treatment of 1000 ppm solution of copper sulfate; (4) DCSA at 0.5 lb/A followed by 24 hours later treatment with 1000 ppm solution of copper sulfate. The plants were rated for percent damage 5 days after treatment.

The results shown in Table 14 demonstrate that DCSA at 0.5 lb/A significantly reduced 1000 ppm copper (Cu) injury on soybeans when applied as a tank mix (TM) or as a pre-treatment at 1 hr or 24 hr before copper treatment. Soybean injury levels were significantly (ANOVA test) reduced from 45% to about 24-33%.

TABLE 14

Enhanced soybean tolerance to copper toxicity by DCSA treatment

| Treatment | Percent injury |
|---|---|
| Cu 1000 ppm | 45.0a |
| DCSA + Cu (TM) | 23.8c |

TABLE 14-continued

Enhanced soybean tolerance to copper toxicity by DCSA treatment

| Treatment | Percent injury |
|---|---|
| DCSA fb Cu (1 hr) | 32.5b |
| DCSA fb Cu (24 hr) | 32.5b |

In an aspect of the present invention, a tolerance to heavy metal toxicity is provided due to improved plant health by DCSA applied to a plant in need of heavy metal toxicity tolerance or DCSA produced in vivo by the action of DMO on dicamba in transgenic plants comprising a DMO transgene.

Example 19

Metabolism of Dicamba to DCSA in Soybeans

Figure 10:
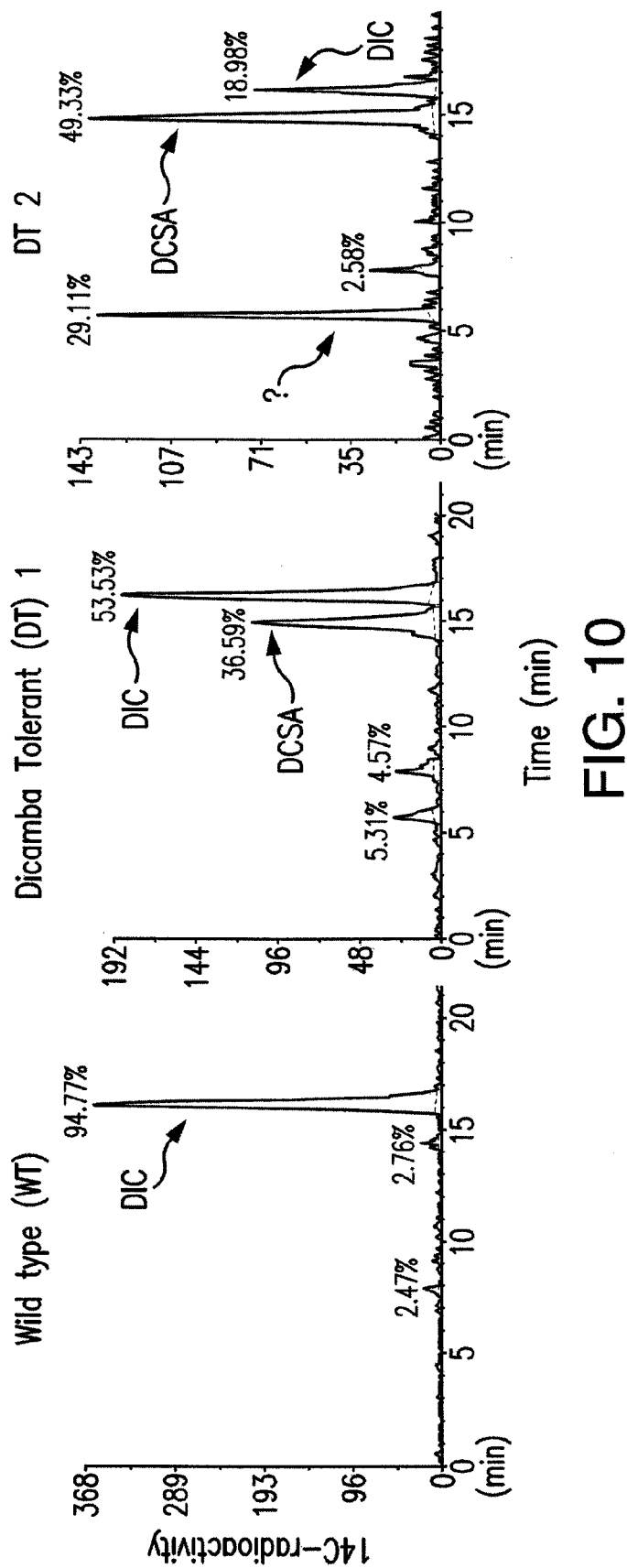
FIG. 10. metabolism of $^{14}$C-dicamba to DCSA in soy leaf strips in 24 hours.

Leaf strip and whole plant studies were performed using liquid chromatography assays to determine metabolism of dicamba to DCSA in soybeans. Leaf tissue was removed from wild-type soybean plants and soybean plants transgenic for the DMO gene and were cut into 1 mm strips, the strips then incubated in 25 mM Tris pH 7.5 with radiolabeled dicamba (14C dicamba) for 24 hours at 30° C. After incubation, the leaf tissue was homogenized with a spinning pestle, acidified, solids pelleted by centrifugation and an aliquot of the supernatant analyzed by RP-HPLC equipped with a radiation detector. As seen in FIG. 10, the radiolabeled dicamba was metabolized to DCSA and other polar metabolites in the transgenic DMO gene containing soybean plants but not in the wild-type soybean plants.

Figure 11:
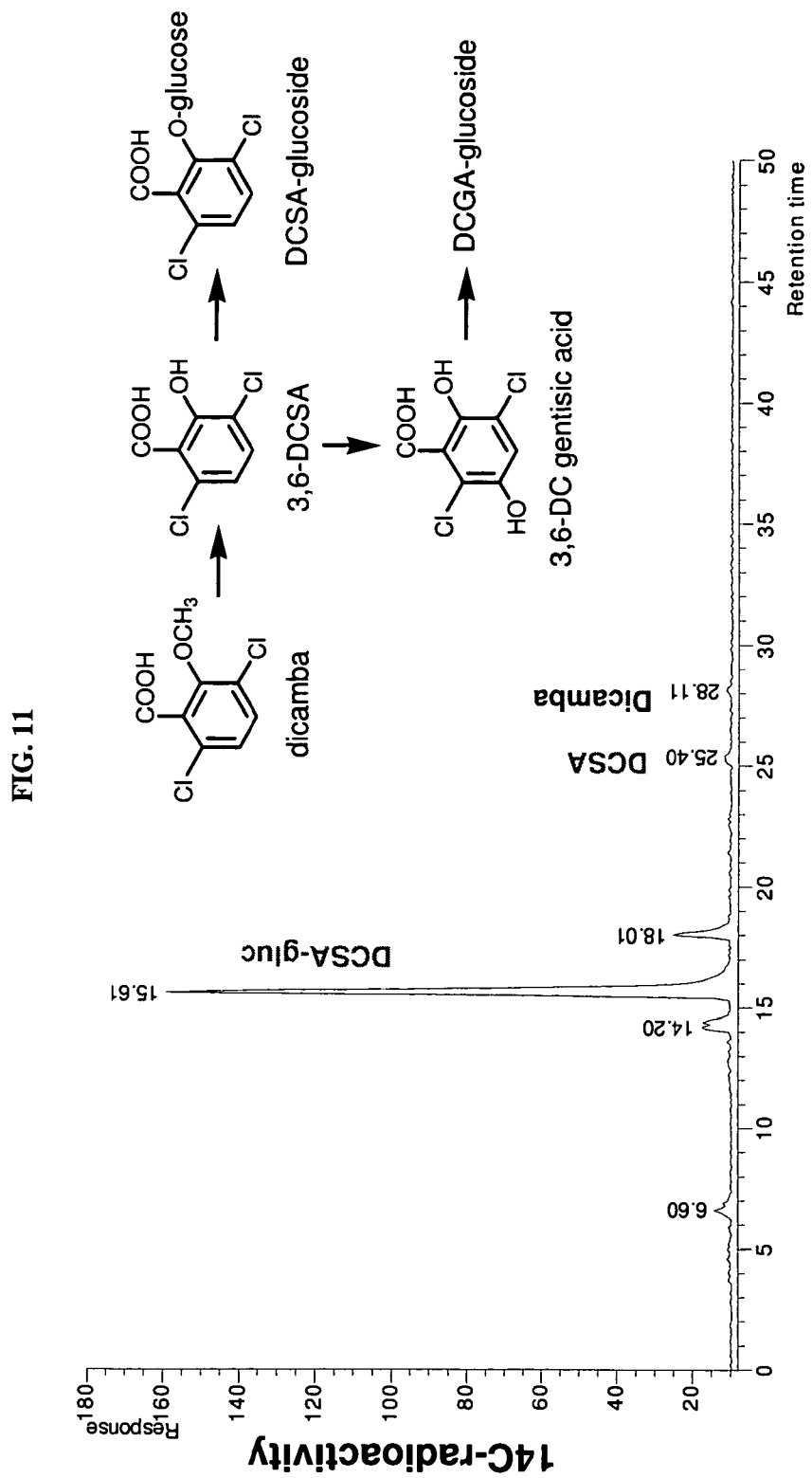
FIG. 11. metabolism of $^{14}$C-dicamba to DCSA and conjugation to glucoside in whole plant studies.

For whole plant assays, soybean plants transgenic for the DMO gene were treated with 14C dicamba by spraying the plants with a solution containing the 14C dicamba at a rate up to 2.5 lb/A. Leaf samples from the treated plants were collected at various times after treatment and analyzed for the DMO metabolites by RP-HPLC. The leaf tissue was homogenized with a spinning pestle, acidified, solids pelleted by centrifugation and an aliquot of the supernatant analyze by RP-HPLC equipped with a radiation detector. As shown in FIG. 11, the whole plant assay demonstrates that in DMO gene transgenic plants DCSA is produced as a metabolite of dicamba.

Residue levels in seeds from plants treated with dicamba at planting and at V3 growth stage were very low (0.04 ppm). Residue levels increased to ~0.1 ppm with R1 application.

\*\*\*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background, or teach methodology, techniques, and/or compositions employed herein.

U.S. Pat. Nos. 4,554,101; 5,004,863; 5,015,580; 5,017,692; 5,159,135; 5,445,962; RE39,247; 5,322,938; 5,352,605; 5,359,142; 5,362,865; 5,378,619; 5,384,253; 5,424,412; 5,508,184; 5,530,196; 5,538,880; 5,550,318; 5,552,299; 5,567,600; 5,591,616; 5,635,055; 5,641,876; 5,659,122; 5,567,862; 5,670,706; 5,689,052; 5,824,877; 5,837,848; 5,846,797; 5,850,019; 5,859,347; 5,981,840; 6,051,753; 6,140,078; 6,160,208; 6,175,060; 6,177,611; 6,232,526; 6,252,138; 6,294,714; 6,384,301; 6,388,170; 6,399,861; 6,403,865; 6,426,446; 6,429,357; 6,429,362; 6,433,252; 6,437,217; 6,624,344; 6,635,806; 7,002,058; 7,022,896; 7,132,528; and 7,151,204

U.S. Patent Publn. 20030115626; U.S. Patent Publn. 20050050587; U.S. Patent Publn 20050022261; U.S. Patent Publn. 20060030488; U.S. Patent Publn 20060162010; U.S. Patent Publ. 20060168700; U.S. Patent Publn. 20060236420.

Allen and Holmes, In: *Photosynthesis: Energy transduction,* 103-141, IRL Press, Oxford, 1986.
Bevan et al., *Nature,* 304:184-187, 1983.
Carrington and Freed, *J. of Virology* 64:1590-1597, 1990.
Chandler et al., *Plant Cell,* 1:1175-1183, 1989.
Chu et al. *Scientia Sinica* 18:659, 1975.
Cork and Khalil, *Adv. Appl. Microbiol.,* 40:289-321, 1995.
Coruzzi et al., *EMBO J.,* 3:1671-1679, 1984.
Depicker et al., *J. Mol. Appl. Genet.* 1:561-573, 1982.
Ebert et al., *Proc. Natl. Acad. Sci. USA,* 84:5745-5749, 1987.
European Patent 553494
European Patent 646643
Frederick et al, *Mycology,* 92:217-227, 2002.
Grossmann, *Trends Plant Sci.* 5:506-508, 2000.
Herman et al., *J. Biol. Chem.* 280:24759-24767, 2005.
Hirschberg et al., *Science,* 222:1346-1349, 1983
Ingelbrecht et al., *Plant Cell,* 1:671-680, 1989.
Kyte and Doolittle, *J. Mol. Biol.,* 157(1):105-132, 1982.
Lawton et al., *Plant Mol. Biol.* 9:315-324, 1987.
Miki et al., In: *Methods in Plant Molecular Biology and Biotechnology,* Glick and Thompson (Eds.), CRC Press, 67-88, 1993.
Murashige and Skoog, *Physiol Plant* 15:473-497, 1962.
Odell et al., *Nature,* 313:810-812, 1985.
PCT Appln. WO 05/102057A2
PCT Appln. WO 97/11086
PCT Appln. WO 97/31115
PCT Appln. WO95/06722
Peterson and Arntzen, In: *Methods in Chloroplast Molecular Biology,* 985-1014, Elsevier Science Publications, B.V., Amsterdam, 1982.
Turner and Foster, *Molecular Biotech.,* 3:225, 1995.
Uknes et al., *Plant Cell,* 4:645-656, 1992.
VanGessel and Majek, 2005, 2005 *Soybean Weed Management Guide: for Delaware and New Jersey*, University of Delaware and Rutgers University
Walker et al., *Proc. Natl. Acad. Sci. USA,* 84:6624, 1987.
Weeks et al., "*Genetic Engineering of Tobacco, Tomato, Arabidopsis, and Soybean Plants for Tolerance to Treatment with the Herbicide Dicamba,*" Soy/2006, 11$^{th}$ Biennial Conference on the Molecular and Cellular Biology of the Soybean, (abstr.), University of Nebraska-Lincoln, Lincoln, Nebr., 2006.
Yang and Russell, *Proc. Natl. Acad. Sci. USA,* 87:4144-4148, 1990.
Zhang et al, *Plant Cell, Tissue and Organ Culture,* 56: 37-46, 1999.

What is claimed is:

1. A method for increasing the germination rate of a seed, comprising:
   (i) contacting the seed with 3,6-dichloro salicylic acid or an analog thereof in an amount that improves the germination rate of the seed as compared to a seed of the same genotype not contacted with 3,6-dichloro salicylic acid or an analog thereof; or
   (ii) contacting a seed with dicamba in an amount that improves the germination rate of the seed as compared to a seed of the same genotype not contacted with dicamba, wherein the seed contacted with dicamba is a transgenic seed comprising a DMO-encoding transgene; wherein the amount that improves the germination rate of the seed is about 0.1 grams to 100 grams of 3,6-dichloro salicylic acid, or an analog thereof, or dicamba per 100 kilograms of seed.

2. The method of claim 1, wherein the seed is in a crop production field.

3. The method of claim 1, further defined as comprising contacting a population of seeds with said dicamba or 3,6-dichloro salicylic acid, or an analog thereof.

4. The method of claim 1, wherein contacting the seed comprises coating the seed with a composition comprising the dicamba or 3,6-dichloro salicylic acid, or an analog thereof.

5. The method of claim 1, wherein 3,6-dichloro salicylic acid, or an analog thereof is 3,6-DCSA, 3,5-DCSA, or 3-CSA, or a metabolite of 3,6-DCSA, 3,5-DCSA, or 3-CSA.

6. The method of claim 1, wherein 3,6-dichloro salicylic acid, or an analog thereof is an analog of DCSA.

7. The method of claim 1, wherein 3,6-dichloro salicylic acid, or an analog thereof is herbicidal and wherein the seed comprises a transgene that encodes DMO.

8. The method of claim 1, wherein 3,6-dichloro salicylic acid, or an analog thereof is not herbicidal.

9. The method of claim 1, wherein the seed is from a dicotyledonous plant.

10. The method of claim 9, wherein the dicotyledonous plant is selected from the group consisting of alfalfa, beans, beet, broccoli, cabbage, carrot, cauliflower, celery, Chinese cabbage, cotton, cucumber, eggplant, flax, lettuce, lupine, melon, pea, pepper, peanut, potato, pumpkin, radish, rapeseed, spinach, soybean, squash, sugarbeet, sunflower, tomato, and watermelon.

11. The method of claim 1, wherein the seed is from a monocotyledonous plant.

12. The method of claim 11, wherein the monocotyledonous plant is selected from the group consisting of barley, corn, leek, onion, rice, sorghum, sweet corn, wheat, rye, millet, sugarcane, oat, triticale, switchgrass, and turfgrass.

13. The method of claim 1, wherein the seed is a seed of a plant tolerant to a herbicide selected from the group consisting of glyphosate, glufosinate, 2,4-D, mesotrione, dithiopyr, isoxaflutole, bromoxynil, atrazine, fluazifop-P, and a sulfonylurea/imidazolinone.

14. The method of claim 13, further comprising contacting the seed with at least one herbicides selected from the group consisting of glyphosate, glufosinate, 2,4-D, mesotrione, thiazopyr, isoxaflutole, bromoxynil, atrazine, fluazifop-P, and a sulfonylurea/imidazolinone.

* * * * *